(12) United States Patent
Grossi de Sa et al.

(10) Patent No.: US 9,012,720 B2
(45) Date of Patent: Apr. 21, 2015

(54) COMPOSITIONS AND METHODS FOR MODIFYING GENE EXPRESSION USING THE PROMOTER OF UBIQUITIN CONJUGATING PROTEIN CODING GENE OF SOYBEAN PLANTS

(71) Applicant: Empresa Brasileira de Pesquisa Agropecuaria, Brasilia-DF (BR)

(72) Inventors: Maria Fatima Grossi de Sa, Brasilia-DF (BR); Luciane Mourao Guimaraes, Brasilia-DF (BR); Joao Aguiar Nogueira Batista, Brasilia-DF (BR); Antonio Americo Barbosa Viana, Brasilia-DF (BR); Rodrigo da Rocha Fragoso, Brasilia-DF (BR); Maria Cristina Mattar da Silva, Brasilia-DF (BR)

(73) Assignee: Empresa Brasileira de Pesquisa Agropecuaria, Brasilia (BR)

( * ) Notice: Subject to any disclaimer, the term of this patent is extended or adjusted under 35 U.S.C. 154(b) by 0 days.

(21) Appl. No.: 13/770,867

(22) Filed: Feb. 19, 2013

(65) Prior Publication Data
US 2013/0152226 A1    Jun. 13, 2013

Related U.S. Application Data

(63) Continuation of application No. 12/017,312, filed on Jan. 21, 2008, now abandoned.

(30) Foreign Application Priority Data

Feb. 5, 2007 (BR) ...................................... 0701172

(51) Int. Cl.
- *A01H 1/00* (2006.01)
- *C12N 15/00* (2006.01)
- *C12N 15/82* (2006.01)
- *C07H 21/04* (2006.01)
- *C07K 14/415* (2006.01)

(52) U.S. Cl.
CPC .................................. *C12N 15/8216* (2013.01)

(58) Field of Classification Search
None
See application file for complete search history.

(56) References Cited

U.S. PATENT DOCUMENTS

| | | | |
|---|---|---|---|
| 5,510,474 A | 4/1996 | Quail et al. |
| 5,614,399 A | 3/1997 | Quail et al. |
| 5,723,765 A | 3/1998 | Oliver et al. |
| 5,753,475 A | 5/1998 | Houck |
| 6,020,190 A | 2/2000 | Quail et al. |
| 6,391,639 B1 | 5/2002 | Schenk et al. |
| 6,441,273 B1 | 8/2002 | Aldwinckle et al. |
| 6,489,462 B1 | 12/2002 | Olszewski et al. |
| 6,528,701 B1 | 3/2003 | Wang et al. |
| 6,670,467 B2 | 12/2003 | Barbour et al. |
| 6,677,505 B1 | 1/2004 | Esnault et al. |
| 6,706,948 B1 | 3/2004 | Albert et al. |
| 2002/0115850 A1 | 8/2002 | Chung et al. |
| 2002/0152501 A1 | 10/2002 | Fischer et al. |
| 2003/0066108 A1 | 4/2003 | Jilka et al. |
| 2003/0175783 A1 | 9/2003 | Waterhouse et al. |
| 2006/0143735 A1 | 6/2006 | Medrano et al. |

FOREIGN PATENT DOCUMENTS

| | | |
|---|---|---|
| WO | WO 8903887 | 5/1989 |
| WO | WO 8910396 | 11/1989 |
| WO | WO 9213956 | 8/1992 |
| WO | WO 9519443 | 7/1995 |
| WO | WO 9713865 | 4/1997 |
| WO | WO 03102198 | 12/2003 |

OTHER PUBLICATIONS

Binet, et al., "Analysis of a sunflower polyubiquitin promoter by transient expression," *Plant Science*, (1991) 79: 87-94.
Callis, et al., "Ubiquitin Extension Proteins of *A. thaliana*," *The Journal of Biological Chemistry*, (1990) 265(21): 12486-93.
Callis, et al., "Ubiquitin and Ubiquitin Genes in Higher Plants," *Oxford Surveys of Plant Molecular & Cell Biology*, (1989) 6: 1-30.
Christensen, et al., "Maize polyubiquitin genes: structure, thermal perturbation of expression and transcript splicing, and promoter activity following transfer to protoplasts by electroporation," *Plant Molecular Biology*, (1992) 18: 675-689.
Clough, et al., "Floral dip: a simplified method for Agrobacterium-mediated transformation of *A. thalianam*" *Plant J.*, (1998)16(6):735-43.
Fraley, et al., "Expression of Bacterial Genes in Plant Cells," *Proc. Natl. Acad. Sci. USA*, (1983) 80:4803.
Fromm, et al., "Expression of genes transferred into monocot and dicot plant cells by electroporation," *Proc. Natl. Acad. Sci. USA*, (1985) 82:5824.
Genschik, et al., "Structure and promoter activity of a stress and developmentally regulated polyubiquitin encoding gene of *Nicotiana tabacum*," *Gene*, (1994) 148: 195-202.
Keil et al., "Both wound-inducible and tuber-specific expression are mediated by the promoter of a single member of the potato proteinase inhibitor II gene family," *EMBO J.*, (1989) 8: 1323-1330.
Keller et al., "Glycine-rich cell wall proteins in bean: gene structure and association of the protein with the vascular system," *EMBO J.*, (1988) 7: 3625-3633.

(Continued)

*Primary Examiner* — Phuong Bui
(74) *Attorney, Agent, or Firm* — Knobbe Martens Olson & Bear LLP

(57) ABSTRACT

A polynucleotide isolated from soybean plants capable of initiating transcription and with sequence identity to SEQ ID No. 1 is provided. In some aspects, the polynucleotide has sequence identity to SEQ ID No. 1 of at least 40%, is the reverse complement or the reverse of such sequences. In some aspects, the polynucleotide is linked to expression enhancers or sequences of interest. In some embodiments, a recombinant vector comprises the polynucleotide. In some aspects, the recombinant vector comprises enhancers, termination sequences, or sequences of interest. In some embodiments a transformed cell, plant, plant part, or propagulum comprise the polynucleotide.

15 Claims, 16 Drawing Sheets

(56) References Cited

OTHER PUBLICATIONS

Keller et al., "Specific expression of a novel cell wall hydroxyproline-rich glycoprotein gene in lateral root initiation," *Genes Devel.*, (1989) 3:1639-1646.

Miles, et al., "Complete nucleotide sequence of the fumarase gene fumA, of *E. coil*," *Nucleic Acids Res.*, (1984) 12(8): 3631-3642.

Paszkowski, et al., "Direct Gene Transfer to Plants" *Embo. J.*, (1984) 3:2717-2722.

Schmülling, et al., "Promoters of the *rolA, B*, and C Genes of *Agrobacterium rhizogenes* Are Differentially Regulated in Transgenic Plants," *Plant Cell*, (1989) 1, 665-670.

Shoemaker, et al., EST Database, Direct Submission, Accession No. BU082665, Jul. 2, 2004.

Tang et al., Gen Embl Database, Direct Submission, Accession No. AF532622, Dec. 3, 2004.

```
Arabidopsis          ------------------------------------------------------------
Uce_Oryza_3          ------------------------------------------------------------
Gos-2_Zea            ------------------------------------------------------------
Uce_Oryza_1          ------------------------------------------------------------
A-Tubulin_Coffea_1   --------------------------------------------AAAAGTTGTAGCGGGA  16
Uce_Oryza_4          ------------------------------------------------------------
UBI9_Saccharum       ------------------------------------------------------------
Enolase_Zea          ------------------------------------------------------------
Actin-2_Zea          ------------------------------------------------------------
Uce_Oryza_2          CTGCAGAAATGCAAATTTCATAAAACAAACTACTAGTACTGTTTGTTCATTGGTCTTATC  60
UceA1.7              ------------------------------------------------------------
UceS8.3              ------------------------------------------------------------
A-Tubulin_Coffea_2   ------------------------------------------------------------
35Sd_AMV             ------------------------------------------------------------

Arabidopsis          ----------------------------------------------------------
Uce_Oryza_3          ----------------------------------------------------------
Gos-2_Zea            ----------------------------------------------------------
Uce_Oryza_1          ----------------------------------------------------------
A-Tubulin_Coffea_1   GGGCTGGACGATGCGTGGAGCGGAAAATGCTGGAGTATTGGACCACCAACCAAACAAAAT  76
Uce_Oryza_4          ----------------------------------------------------------
UBI9_Saccharum       ----------------------------------------------------------
Enolase_Zea          ----------------------------------------------------------
Actin-2_Zea          ----------------------------------------------------------
Uce_Oryza_2          CAAAACTTAGCCACTGCAACAAGTTCTTGAACCTTAGCACAATCATATTGTGCATGCACT 120
UceA1.7              ----------------------------------------------------------
UceS8.3              ----------------------------------------------------------
A-Tubulin_Coffea_2   ----------------------------------------------------------
35Sd_AMV             ----------------------------------------------------------

Arabidopsis          ------------------------------------------------------------
Uce_Oryza_3          ------------------------------------------------------------
Gos-2_Zea            ------------------------------------------------------------
Uce_Oryza_1          ------------------------------------------------------------
A-Tubulin_Coffea_1   AGTTTTAGTATATGGGGTTTCGAACTTTCCAGTCAACCTACAACAATCTGCTTCTATAAA 136
Uce_Oryza_4          ------------------------------------------------------------
UBI9_Saccharum       ------------------------------------------------------------
Enolase_Zea          ------------------------------------------------------------
Actin-2_Zea          ------------------------------------------------------------
Uce_Oryza_2          TGTTTATTGCAAAGAATGGTGCGTAGGGAACACGCATGATTTTTGAATTGCTGGCACATA 180
UceA1.7              ------------------------------------------------------------
UceS8.3              ------------------------------------------------------------
A-Tubulin_Coffea_2   ------------------------------------------------------------
35Sd_AMV             ------------------------------------------------------------

Arabidopsis          ------------------------------------------------------------
Uce_Oryza_3          ------------------------------------------------------------
Gos-2_Zea            ------------------------------------------------------------
Uce_Oryza_1          ------------------------------------------------------------
A-Tubulin_Coffea_1   CAATAATAAAAGAGTAATTAAATTACTGGTAGCGTTGGTGTATTTGGATTTGCCAGCTTT 196
Uce_Oryza_4          ------------------------------------------------------------
UBI9_Saccharum       ------------------------------------------------------------
Enolase_Zea          ------------------------------------------------------------
Actin-2_Zea          ------------------------------------------------------------
Uce_Oryza_2          ATTTTATCATTAGAAACTGGAATGCAACATGTACCCTTTGTCATGGCTTTCTTTCCGAGAC 240
UceA1.7              ------------------------------------------------------------
UceS8.3              ------------------------------------------------------------
A-Tubulin_Coffea_2   ------------------------------------------------------------
35Sd_AMV             ------------------------------------------------------------
```

FIGURE 4A

```
Arabidopsis              ------------------------------------------------------------
Uce_Oryza_3              ------------------------------------------------------------
Gos-2_Zea                ------------------------------------------------------------
Uce_Oryza_1              ------------------------------------------------------------
A-Tubulin_Coffea_1       GCTTCCAAACTCATATCATCAATTTGATAGCACTTGGATACGGAGATCGCTTTTGTCTGC 256
Uce_Oryza_4              ------------------------------------------------------------
UBI9_Saccharum           ------------------------------------------------------------
Enolase_Zea              ------------------------------------------------------------
Actin-2_Zea              ------------------------------------------------------------
Uce_Oryza_2              ATTGCACTGTTTTTTTTAATCCTATCATTATCATAATGCCAAGAACTGGTCACCAACCAG 300
UceA1.7                  ------------------------------------------------------------
UceS8.3                  ------------------------------------------------------------
A-Tubulin_Coffea_2       ------------------------------------------------------------
35Sd_AMV                 ------------------------------------------------------------

Arabidopsis              ------------------------------------------------------------
Uce_Oryza_3              ------------------------------------------------------------
Gos-2_Zea                ------------------------------------------------------------
Uce_Oryza_1              ------------------------------------------------------------
A-Tubulin_Coffea_1       CTTAGTATGATATGATTGCTCACCCGCTGTAGACATGATTTAAAGGAAAATAACACAAAT 316
Uce_Oryza_4              ------------------------------------------------------------
UBI9_Saccharum           ------------------------------------------------------------
Enolase_Zea              ------------------------------------------------------------
Actin-2_Zea              ------------------------------------------------------------
Uce_Oryza_2              CATTTTGCATCATGGTTAGTTGAGCTGTCCCCATGTATCAATAGGTGCATTGTATTGGTC 360
UceA1.7                  ------------------------------------------------------------
UceS8.3                  ------------------------------------------------------------
A-Tubulin_Coffea_2       ------------------------------------------------------------
35Sd_AMV                 ------------------------------------------------------------

Arabidopsis              ------------------------------------------------------------
Uce_Oryza_3              ------------------------------------------------------------
Gos-2_Zea                ------------------------------------------------------------
Uce_Oryza_1              ------------------------------------------------------------
A-Tubulin_Coffea_1       ATATATATATAAGACCAACAAATTATAACTGAAAACTTTTCAGTAATGTTAATTCTAACA 376
Uce_Oryza_4              ------------------------------------------------------------
UBI9_Saccharum           ------------------------------------------------------------
Enolase_Zea              ------------------------------------------------------------
Actin-2_Zea              ------------------------------------------------------------
Uce_Oryza_2              CAAAATATAAATGCAGTGGATGCAACCTATCTCATGGCCGTCAACAAAAGAAATCAAAAG 420
UceA1.7                  ------------------------------------------------------------
UceS8.3                  ------------------------------------------------------------
A-Tubulin_Coffea_2       ------------------------------------------------------------
35Sd_AMV                 ------------------------------------------------------------

Arabidopsis              ------------------------------------------------------------
Uce_Oryza_3              ------------------------------------------------------------
Gos-2_Zea                ------------------------------------------------------------
Uce_Oryza_1              ------------------------------------------------------------
A-Tubulin_Coffea_1       CATGTGACTAGACCTGCTATCATCAGCTGCAATTCTAGAGGAAACTTGGACCAGATCAGA 436
Uce_Oryza_4              ------------------------------------------------------------
UBI9_Saccharum           ------------------------------------------------------------
Enolase_Zea              ------------------------------------------------------------
Actin-2_Zea              ------------------------------------------------------------
Uce_Oryza_2              GGAAATGCACCATCTTATATCTCCAGTTTATATGAACAGATTGGATAAGATCATAAGATC 480
UceA1.7                  ------------------------------------------------------------
UceS8.3                  ------------------------------------------------------------
A-Tubulin_Coffea_2       ------------------------------------------------------------
35Sd_AMV                 --------                                        ------------
```

FIGURE 4B

```
Arabidopsis        ------------------------------------------------------------
Uce_Oryza_3        ------------------------------------------------------------
Gos-2_Zea          ------------------------------------------------------------
Uce_Oryza_1        ------------------------------------------------------------
A-Tubulin_Coffea_1 AGTTGTAAAGGGCTGCAGTCCATTCCTGCACTATTCAGTTTGCAGGTAGATGGGTGGACC  496
Uce_Oryza_4        ------------------------------------------------------------
UBI9_Saccharum     ------------------------------------------------------------
Enolase_Zea        ------------------------------------------------------------
Actin-2_Zea        ------------------------------------------------------------
Uce_Oryza_2        AAGTGGTTTATATTATTTTGAGGAATATAACATGGATTCATCCTAATCACTCGTCTAGGC  540
UceA1.7            ------------------------------------------------------------
UceS8.3            ------------------------------------------------------------
A-Tubulin_Coffea_2 ------------------------------------------------------------
35Sd_AMV           ------------------------------------------------------------

Arabidopsis        ------------------------------------------------------------
Uce_Oryza_3        ------------------------------------------------------------
Gos-2_Zea          ------------------------------------------------------------
Uce_Oryza_1        ------------------------------------------------------------
A-Tubulin_Coffea_1 ATTATATGGATCTGGTCCAGCGTGAATGCAGTTGTAGTAAAGACATGTTGGATTTGTTAT  556
Uce_Oryza_4        ------------------------------------------------------------
UBI9_Saccharum     ------------------------------------------------------------
Enolase_Zea        ------------------------------------------------------------
Actin-2_Zea        ------------------------------------------------------------
Uce_Oryza_2        AGTATGTGTATTCATGATGGATATGGTACTATACTACGGAGTTTTTTCTTCACAAAATAA  600
UceA1.7            ---------------------------------AGTGAAGTAGCAGAGATAATAG       22
UceS8.3            ------------------------------------------------------------
A-Tubulin_Coffea_2 ------------------------------------------------------------
35Sd_AMV           ------------------------------------------------------------

Arabidopsis        ------------------------------------------------------------
Uce_Oryza_3        ------------------------------------------------------------
Gos-2_Zea          ------------------------------------------------------------
Uce_Oryza_1        ------------------------------------------------------------
A-Tubulin_Coffea_1 GGATCAAACTACTACTAGTAGGGAAATGCTTCAAAGACTTCTCTTGTGATTTTCTCCCAG  616
Uce_Oryza_4        ------------------------------------------------------------
UBI9_Saccharum     --------------------GAATTCCGGCGTGGGCGCTGGGCTAGTGCTCCCGCAGCGA   40
Enolase_Zea        ------------------------------------------------------------
Actin-2_Zea        ------------------------------------------------------------
Uce_Oryza_2        CCTGTTATTTTGACCTCCAACCAAACACGAATTATACCAAAAATTGGGTTATTTCATCTA  660
UceA1.7            TTATTACAGTAGCAGTAATAAAATAAAATACATTTTATTACAAAAAAACGTACAAGAGGT   82
UceS8.3            -----------------------------TGTGTAGAAGCAGAGAAAACCAAAAGAGTAG   31
A-Tubulin_Coffea_2 ------------------------------------------------------------
35Sd_AMV           ------------------------------------------------------------

Arabidopsis        ------------------------------------------------------------
Uce_Oryza_3        ------------------------------------------------------------
Gos-2_Zea          ------------------------------------------------------------
Uce_Oryza_1        ------------------------------------------------------------
A-Tubulin_Coffea_1 CCGAATGGTCCAAGTACACTAGCAAAAGAAGCACAAACGGTACCAATGACTCGAGCGAGC  676
Uce_Oryza_4        ------------------------------------------------------------
UBI9_Saccharum     GCGATCTGAGAGAACGGTAGAGTTCCGGCCGGGCGCGCGGCACACGAGGAGGGTCGGGCG  100
Enolase_Zea        ------------------------------------------------------------
Actin-2_Zea        ------------------------------------------------------------
Uce_Oryza_2        TAGTACAACTCTATTATAAACATGCAGTAAATTATCCTACACATATACCAAAATTCAAGT  720
UceA1.7            CCGCGAAGATAGCCAATGAGAACCCAAGAAGACAACCCAATTCT-CCTATTTTTTTATTA  141
UceS8.3            TGAGGAAGCCCACTTACTTCAAGGACTTTGTCTAAAGGGTGAAGTGTGTATTCCATAAC   91
A-Tubulin_Coffea_2 ------------------------------------------------------------
35Sd_AMV           ------------------------------------------------------------
```

FIGURE 4C

```
Arabidopsis          ------------------------------------------------------------
Uce_Oryza_3          ------------------------------------------------------------
Gos-2_Zea            ------------------------------------------------------------
Uce_Oryza_1          ------------------------------------------------------------
A-Tubulin_Coffea_1   TGACATTTTGGGCTTCAGATTAGCACAAGACAAAAGGATTTTTCACTTTTCTTCTGTAGG 736
Uce_Oryza_4          ------------------------------------------------------------
UBI9_Saccharum       GGGAGGATCCGATGGCCGGGAACGAGTGGATCAATGGGTACCTGGAGGCGATCCTCGACA 160
Enolase_Zea          ------------------------------------------------------------
Actin-2_Zea          ------------------------------------------------------------
Uce_Oryza_2          GTAATAATCCTAATACACAGACTTAAAAATCAAACTATTTCCTTTTTAAGATATCGAAAA 780
UceA1.7              AATATTTCTAGAAGAAAGGGTAAATTACGCCCCACGGTCACAAAACTATTAATAAGATCA 201
UceS8.3              AAAATCATCAACAAACAAATTCTGTTACTAGGATTACTATAAATACAATTGTAATAAACA 151
A-Tubulin_Coffea_2   --------------CATTTCTTGCCAGAAAGCACTAGTGAATATTCTATCCCTGTCAG 44
35Sd_AMV             ------------------------------------------------------------

Arabidopsis          ------------------------------------------------------------
Uce_Oryza_3          ------------------------------------------------------------
Gos-2_Zea            ------------------------------------------------------------
Uce_Oryza_1          ---------------------GTCGACCTGATGATTATTTGTTGATCATGATTTTCTTT 39
A-Tubulin_Coffea_1   TGATCCTGGACTCGCAGGTTGGCATGCTCAATTCAGGAGCTTTTGAGATTGGATAGGGTG 796
Uce_Oryza_4          ------------------------------------------------------------
UBI9_Saccharum       GCCACACCTCGTCGCGGGGTGCCGGCGGCGGCGGCGGCGGGGGGGACCCCAGGTCGCCGA 220
Enolase_Zea          ------------------------------------------------------------
Actin-2_Zea          ------------------------------------------------------------
Uce_Oryza_2          CCATTTTTTTAACGGAAGGAAAACAAATTCGGGTCAAGGCGGAAGCCAGCGCGCGCCACCCC 840
UceA1.7              TATATTTATCACTCAACTTCCAAAAGTTACAAAATGATTATTAAACTATTCAAAAGTTTT 261
UceS8.3              AGCAAAGATATGAATGAATGAAATTTCCATATTTCTTACTTTTCTTCTTTGGAGGGTTCT 211
A-Tubulin_Coffea_2   TCACTATAGATTCTGGAAGTCCATGTAATCTAAAAATGTTTCCAGGAAGAGTTGAGCCAC 104
35Sd_AMV             ------------------------------------------------------------

Arabidopsis          ---------GTGTTCATTTGATAGAGTCTAAAATCACCACTTACATTGACTAACCCCAA 50
Uce_Oryza_3          ------------------------------------------------------------
Gos-2_Zea            ------------------------------------------------------------
Uce_Oryza_1          TGGCTATTTGATTTTTTGAAAGATATTTTTTTCCCTGGGAAGACACCTATGGGACGAAGA 99
A-Tubulin_Coffea_1   TTCCTTATGAATGCACCGCAGGTTGCATGCTCAATTCAGAGCCCTTCACATGTAACCGTG 856
Uce_Oryza_4          ------------------------------------------------------------
UBI9_Saccharum       CGAAGGCGGCGAGCCCCCGCGGC-GCGCACATGAACTTCAACCCCTCGCACTACTTCGTC 279
Enolase_Zea          ------------------------------------------------------------
Actin-2_Zea          ------------------------------------------------------------
Uce_Oryza_2          ACGTCAGCGAATACGGAGGCGCGGGGTTGACGGCGTCACCCGGTCCTAACGGCGACCAAC 900
UceA1.7              ATTTCAAGTCATTGGATTGTTAAAATAGCATTTGTATGGATTTCCCTGTTCACATTGCCT 321
UceS8.3              CGTCCTCGAAACCAAATTCTTAGTTCTCTTACCAATTTGTCTCTTTTTGGTTGGTTATTC 271
A-Tubulin_Coffea_2   CTGTTTGGTTGTGAAGGGGTGAGCTAAGGCAAGCAAATGACCTACTTTGGACAACCTATC 164
35Sd_AMV             ------------------------------------------------------------

Arabidopsis          AAATTTGTCCTAAACACTAATCAATCCGAAGATTATAAAATGTCGACAAAGAAAATAAAA 110
Uce_Oryza_3          ------------------------------------------------------------
Gos-2_Zea            ------------------------------------------------------------
Uce_Oryza_1          TATTATGTTATATATATATATATATATATATATATATATATATATATATATATATATATA 159
A-Tubulin_Coffea_1   TGTAGCCCAGGCCCAAATGCCCCGGAAYTTTAAACTGAAATCTCGGAAYAGCAGATGGCA 916
Uce_Oryza_4          ------------------------------------------------------------
UBI9_Saccharum       GAGGAGGTGGTCAAGGGCGTCGACGAGAGCGACCTCCACCGGACGTGGATCAAGGTCGTC 339
Enolase_Zea          ---------------------------------------------TCATATATTTATG 13
Actin-2_Zea          --------------------------------------------------TCAGT 5
Uce_Oryza_2          AAACCAGCCAGAAGAAATTACAGTAAAAAAAAGTAAATTGCACTTTGACCCACCTTTTAT 960
UceA1.7              ACATCAATCGAAGCCTCTCATTCCCCTTCTTTTTTATAGATTAAGTTTTTTTTTATAAAA 381
UceS8.3              AGTGTAACAAAATAAAAAAAATAAGAATTATGAATCTAAATAATGGTATACATGACAAAG 331
A-Tubulin_Coffea_2   AATCACGTATTATATCCTTGAGATTCTGGAAGGCTCTCTATGAAGTCCATGGTTAGGTGA 224
35Sd_AMV             -----------------------------------------------GGTCCGATCTGAG 13
```

FIGURE 4D

```
Arabidopsis        TAAAATAGGAGTCTATGAGTCGATGGAACTTATCCAACTAAACTTTAATAAGAATGAACC 170
Uce_Oryza_3        ------------------------------------------------------------
Gos-2_Zea          ------------------------------------------------------------
Uce_Oryza_1        TATATATCACATCAGTCTCTGCACAAAGTGCATCCTGGGCTGCTTCAATTATAAAGCCCC 219
A-Tubulin_Coffea_1 ACGGTCGTAATTCGTCAAGCAATCCGAAACGTCGCCACACCCCCACGCCAGCTGGAAAAT 976
Uce_Oryza_4        ---------------------------AAGCTTGTCTGTCTCTACTAGATACCAGGGTTTC 34
UBI9_Saccharum     GCCACCCGCAACGCCCGCGAGCGCAGCACCAGGCTCGAGAACATGTGCTGGCGGATCTGG 399
Enolase_Zea        AACGGAGATAGTGCATCTATCATGCGATTCTTCGACGGAGTCGACGTCTGATTGGACCAG 73
Actin-2_Zea        ATGATTGCTTTCAATATAGGCTGATGGAGCCTATGAATGATCTATAACTATGTGATTGGA 65
Uce_Oryza_2        TACCCAAAGTTTCAATTTGGACCACCCTTAAACCTATCTTTTCAAATTGGGCCGGGTTGT
1020
UceA1.7            CAATTTTAAACATCATGAATCTCTGAACTAAAATTTAAATAACTTTTTTCTTCGATCTTT 441
UceS8.3            AGATATAGCTCACATTGACAACTAAAAATTGAATTACTAATCACTTGCATTTTCATTTAT 391
A-Tubulin_Coffea_2 GTCCAAGCTAAACGAGGAATAGGTGATGGTTGTAGCAGTCCAAGGTAGGGTCCATGCTTT 284
35Sd_AMV           ACTTTTCAACAAAGGGTAATATCGGGAAACCTCCTCGGATTCCATTGCCCAGCTATCTGT 73

Arabidopsis        AAACTCAATTTT--GTAATAATATTTAAAATACGTT---TTTACTCTCTCCCAGA---AT 222
Uce_Oryza_3        ------------------------------------------------------------
Gos-2_Zea          ------------------ATTATTGGCTGTAGGAT---TCTAAACCGAGCCTAA---AT 35
Uce_Oryza_1        ATTCACCACATT--TGCGAGATAGTCGAAAAGCACCA--TCAATATTGAGCTTCAGGTAT 275
A-Tubulin_Coffea_1 CAGTTCAAAATT--CAAAATTCATTTGGAGCCGTTC---AAACAAAATTGTTTCAGTTTT
1032
Uce_Oryza_4        ATCTTTCGGTTT--GGTCATTTGGACCAGGGTGCCCG--AAATATCGAAATTTCAGAAAT 90
UBI9_Saccharum     CACCTCGCGCGCAAGAAGAAGCAGCTGGAGCTGGAGG--GCATCCAGAGAATCTCGGCAA 457
Enolase_Zea        AATTTCAGATGGTGAGCAAAAGTGCCACTTGCCTGCC--TCCTTTTCTCGTGCCTGCCTC 131
Actin-2_Zea        TGTCTTAACTTGCCTAGCCAAGCTCGTATGAGCCTCT--TTTACTGGGTACCACTAATTT 123
Uce_Oryza_2        GGTTTGGACTACCATGAACAACTTTTCGTCATGTCTAACTTCCCTTTCGGCAAACATATG
1080
UceA1.7            GACATTGAATGTTAAAATTAACTTGAATCTAAGGTATG-TTCTACTTGTTGATAAACACAG 500
UceS8.3            CTTTTACACCAGCGACAACCAAATTGATCATACAACATTTGAACCAACTTTTCATGTTTA 451
A-Tubulin_Coffea_2 GACTTAAATCTTTGGCATATGTCACAAGCATGAATATACCTGATGATTTTCCCCAAATGT 344
35Sd_AMV           CACTTCATCAAAAGGACAGTAGAAAAGGAAGGTGGCACCTACAAATGCCATCATTGCGAT 133

Arabidopsis        ATCCCATCTCTCTGATTCCAATTCCTCCTCTCTCTCT---TTCGTCTCTCTAC------- 272
Uce_Oryza_3        ------------------AAGCTTTGCTCCGTGTCT---GCTTGGGCCATAT------- 31
Gos-2_Zea          AGCTGGAATAGCT--CTATAGCCCTCAATCCAAACTA---ATGATATCTATAC------- 83
Uce_Oryza_1        TTTTGGTTGTGTTGTGGTTGGATTGAGTCCGATATAT---ACCAAATCAATATA----AT 328
A-Tubulin_Coffea_1 GCCCCTCGCCTGCTGCCCTAATCTTACCCCGCCATTG----GGGCTTGGATTACTC---GC
1086
Uce_Oryza_4        TTCGGTTCGAAATTATATGAATTTTTGAACAAAATTT---GATTAAATTAAACAA----AA 144
UBI9_Saccharum     GAAGGAAGGAACAGGAGCAGGTGCGTCGTGAGGCGAC---GGAGGACCTGGCCGA---GG 511
Enolase_Zea        AAGGATAGAAAGAAAGGAGAAACAATATACTATTTAA---GATCAGATAAAATAT---TA 185
Actin-2_Zea        CTATATATTAGATACAGTTAAATA---AGTCTAAACTA---CATCGGTGCGTGCG----TG 174
Uce_Oryza_2        AACCATATATAGAGGAGATCGGCCGTATACTAGAGCT----GATGTGTTTAAGGTC---GT
1134
UceA1.7            ATCCATCGTGTTGATCATTGAATCGTCACTTGGAGCT---CACTCATCGGACTTAAA-AA 556
UceS8.3            ATTTTCTATGTGTAACCATATACTGCATAGAGGACCA---TACATGTACCTTTTGCATGG 508
A-Tubulin_Coffea_2 TTTTGAGGTTTTTAATACCGGGAATGGCCCAGGAAAAGGGCCCTGGCTTTGCACCAAGG 404
35Sd_AMV           AAAGGAAAGCCTATCGTTCAAGATGCCTCTGCCGACAGTGGTCCCAAAGATGGAC---CC 190

Arabidopsis        CCCGAATTGATTGTTTTAACCCCCGGTGATCGGAGCAAACTCT--CTGACGGTGACCGCC 330
Uce_Oryza_3        AC----ACGGACCAGCCCAATAGCCAGAAGCCTGT---AGCTCT--CC-ATGG-----GCC 77
Gos-2_Zea          TTATGCAACTCTAAATTTTTATTCTAAAAGTAATATTTCATTT--TTGTCAACGAGATTC 141
Uce_Oryza_1        TCACTACGGAATATACCATAGCCATCACAACTTTATTAATTTTGGTAGCTTAAGATGGTA 388
A-Tubulin_Coffea_1 TCCAGTCTATATATATAACTCCCTCCCGCATTGCCTCACCACACGACCCCAAGTCCTCTC
1146
Uce_Oryza_4        TATTATCAGATTTGCAAAAAATATGAAAAAAAATCGGTCGAAATAATGTCGTATCTGGG 204
UBI9_Saccharum     ATCTGTCAGAA-GGCGAGAAGGGAGACACCATCGGCGAGCTTGCGCCGGTTGAGAC-GAC 569
Enolase_Zea        TAAGTCAAGGATAGAAAGAAAGGAGAAACAATATACTATTTAAGATCAGATAAAAAAGA 245
Actin-2_Zea        CCAGTACGACTAGATGTAGTCAACTAAACACAGGTTAAGCTGTGATCAATGTA---TGTA 231
Uce_Oryza_2        TGATTGCACGAGAAAAAAAAATCCAAATCGCAACAATAGCAAATTTATCTAGTTCAAAGT
1194
UceS8.3            TGCATACACCTCTAACTTATATTCTGAAACAAGTTTAGTTTCTATTTGCTAGTGTTGTA 568
A-Tubulin_Coffea_2 TCCCCTAAGAATTTCTGGCAAAAGTTCAAGCGCGTTCCAAAGTGCCCCAATGGGACCTCTC 464
35Sd_AMV           CCACCCACCAGGAGCATCCTCCAAAAACAAGACGTTCCAACCACGTCTTCAAAGCAAGTG 250
```

FIGURE 4E

```
Arabidopsis         GGTGATC--ATTT-TTTGTGAACTTCACTTT---TGGTAAGCAGCTT--TGACTTT-TGT 381
Uce_Oryza_3         CGTACTC--GTGC-CACGTG----TCAATCC---TGTGGTTCGGTTTCGTGGCGGT-TGC 126
Gos-2_Zea           TCTACTCT-ATTC-CACAATCTTTTGAAGCTATATATTTACCTTAAATCTGTACTCTA-TAC 198
Uce_Oryza_1         TATATAAT-AACC-AATTAACAACTGATTCTAATTTTACTACGGCCCAGTATCTAC-CAA 445
A-Tubulin_Coffea_1  CTTCTTCTCCTTT-CCCAGATCTCGGAGGTCTCTCACTCTTCCGATCCAGAGACGT-CTT
1204
Uce_Oryza_4         TTCGATCCGAAAT-TTTGAACCCATGCTAGCTGCCAGGCTTTGGATTCTGAGCGTCACGT 263
UBI9_Saccharum      CAAGAAGAAGTTC-CAGAGGAACTTCTCTGACCTTACCGTCTGGTCTGACGACAAT-AAG 627
Enolase_Zea         GCTAATA--ATTT-TTTGGGACACATATACTGGTTACATTGTTATAATCTGTATATATCA 302
Actin-2_Zea         GAGAGTCTGACTC-TTTATATGCGGACAACTAAACACACGATAAGTGTCGAGAATGATTG 290
Uce_Oryza_2         GAAAAGATATGTT-TAAAGGTAGTCCAAAGTA---AAACTTAGGGGCTGTTTCGTTCCCA
1250
UceS8.3             CACAATCAAATTTGTTCTTATCATTCTTTTTTTTGTGTGAAAGTTACATTCTTAAATAA 628
A-Tubulin_Coffea_2  CAAAAAGGTGCCCCGGGGACAAGTTGTGCTCAGTTCGGCGCGTTTCAAGACAGGTTTTG 524
35Sd_AMV            GATTGATGTGATGGTCCGATCTGAGACTTTTCAACAAAGGGTAATATCGGGAAACCTCCT 310

Arabidopsis         TC-ATAATCCT-TCACTTTTACTTT----TCAATTTT-GCTTTTTCC-TCTG----ATCT 429
Uce_Oryza_3         GT-TTCCTCCTCTCTCTTTTCTTTT----TCATCTTT-TTTTTTTCT-TACG----ACAT 175
Gos-2_Zea           CA-ATAATCAT--ATATTCTATTAT----TTATTTTTATCTCTCTCC-TAAGGAGCATCC 250
Uce_Oryza_1         TACAAAACAACGAGTATGTTTTCTT----CCGTCGTAATCGTACACAGTACAAAAAAACC 501
A-Tubulin_Coffea_1  TGTATACGCCTCTGGTATCTCCATT----CCTCCTTTTTCCCTCTCTTCCAAAAATCTCC
1260
Uce_Oryza_4         CAGGCACAATAAAATATTTGGGCCT----CTAACTCTTCGTGGGCTGATCTGGGCCGTAG 319
UBI9_Saccharum      GAGAAGAAGCTTTACATTGTGCTCA----TCAGCGTG-CATGGTCTTGTTCGTGGAGAAA 682
Enolase_Zea         CG-TTGTTCGAATATATTCCAAATT----TTTACTATGATTCGTGCTCTACCGGAACTAC 357
Actin-2_Zea         AGGAAATATTGGTCGTTCCACGTGA----TTGAGTAAGAATGAGAGGGAAATAAAAGGAT 346
Uce_Oryza_2         GCCATACTTTACCATTACTTGCCAA----CAAAAGTTGCCACACCTTGTCTAAGGTGAGG
1306
UceS8.3             GTATTATGGAATAAGCTTTCATATTAC--TTAACTTTATTTCTTACTCGTTATTTCAAAA 686
A-Tubulin_Coffea_2  GCCAGAAAGCAAGGGGTTCCAAAGGG--TGTCAGAGGGTCCATGTTTCAAAACTCCGGG 582
35Sd_AMV            CGGATTCCATTGCCCAGCTATCTGTCACTTCATCAAAAGGACAGTAGAAAAGGAAGGTGG 370

Arabidopsis         GATCTTAGTT-----ATTAAGCTGTTGAATCGCATGATCCTTTC----TTCTCTGATTGA 480
Uce_Oryza_3         T-TATAGGTT-----TCGTAGCGGCTGCGTTTCCTATTTTCCTT----TTCTTTTTCTAT 225
Gos-2_Zea           CCCTATGTCT-----GCATGGCCCCCGGTCGGGTCCCAATCTC----TTGCTCTGCTAG 301
Uce_Oryza_1         TGGCCAGCCT-----TTCTTGGGCTGGGGCTCTCTTTCGAAAGG----TCACAAAACGTA 552
A-Tubulin_Coffea_1  TATTCATTTC-----TCAAAACATCGCGAAAATGAGAGAGTGCA----TCTCCATCCATA
1311
Uce_Oryza_4         CAGACGAGAG-----ACGCCATGACACGATCTCATCAATTCCGTAG--TGGCCACGGAAC 372
UBI9_Saccharum      ACATGGAACT-----AGGTCGTGATTCTGATACAGGTGGCCAGGTGAAATATGTGGTCGA 737
Enolase_Zea         TTCTAGATTT-----TGAAAACTTTATGAGAATTTTCTTATTTAG---ATACACTAAGGC 409
Actin-2_Zea         TTGGTGCGTTG---GTTTTGAAGGCAGGATTTGGTTAGGATGGGTGGACGTTTGAAGTGA 403
Uce_Oryza_2         TGATCAAATTGTTAGCCACAACTTACTAAGCCTAAGGGAATCTTGCCACACTTTTTTGAG
1366
UceS8.3             GGTGAAAATTAC--ATTTCTACCCAGACACACACTAAATACAGTACAAACTCGAAGCAAA 744
A-Tubulin_Coffea_2  TGTCTTGGTCCCCCATAATTGACTTCGGCTAAGTAAAGGAAAACCT--TAGCCGAGGCTG 640
35Sd_AMV            CACCTACAAATGCCATCATTGCGATAAAGGAAAGGCTATCGTTCAAGATGCCTCTGCCGA 430

Arabidopsis         TTATTTCTAATCCTTC----ATGGGTT--TTATGACGAA-TCGTGTGTTAGGGATTCGTTT 534
Uce_Oryza_3         TTATTTTTATGGGATA---TTCGCTT--TCGTGGCGG--CTGCGTTTCCTCG---CCCAT 275
Gos-2_Zea           TAGCACAGAAGGGACA---CTAGA--------AATGAC-TTGCTTGACTTAGAGTATCAG 349
Uce_Oryza_1         CACGGCACTAACGCCC---TTTGCTGCGTGTTAACGG--CCACCAACCCCGCCGTGACGA 607
A-Tubulin_Coffea_1  TTGGTCAGGCCCGGTAT---CCAGGTCGGAAATGCCTG--CTGGGAGCTCTACTGCCTCGA
1366
Uce_Oryza_4         TCACGTAGCGCAAATG---CCGCTCCCGTTTCCGCATC-GTGCGATTTATCTCCTTTCTG 428
UBI9_Saccharum      ACTTGCAAGAGCGATG---TCAATGATGCCTGGAGTGT-ACAGGGTGGACCTCTTCACTC 793
Enolase_Zea         TAATTTTGGTTGGTTT---TTGGCTCGCTAGCTACCA--TTACCTCCTGCATCTAGACAT 464
Actin-2_Zea         TGAGTTTTTCAAGCGT---ATAGATTTTCTATTTGTCC-TTTTTAATTAACTTTCTCCCA 459
Uce_Oryza_2         CCATTGACACGTGGGA---GTGAATTTGTTAGAGGGAA-AT-CTTGCCACAACTGTGGCT
1421
UceS8.3                                              TCACAAGGGCAAGGGGTGGAATATAAAGA 804
A-Tubulin_Coffea                                   CGAACGG--CCAGGGTGGTCGGAGCCTAAG 696
35Sd_AMV                                            AGGAGCA-TCGTGGAAAAAGAAGACGTTC 489
```

FIGURE 4F

```
Arabidopsis         TTTCTGGGTTGGGTTTCTAAATTTGTTGGT-CTAAGAACAGTGAAAT-----TGTTGTTT 588
Uce_Oryza_3         ATATAAGAGCGGGTGACCACGACTGC--------GGCGCGGCGCA---------CCACTC 318
Gos-2_Zea           ATA-AACATCATGTTTACTTAACTTTAAAT-TTGTATCGGTTCTAC------TATTTTTA 402
Uce_Oryza_1         A-ACGGCATCAGCTTTCCACCTCCTCGATA-TCTCCGCGGCGCCGTC-----TGGACCCG 660
A-Tubulin_Coffea_1  GCACGGCATCCAGGTAAATTGCCTTCTATC-TAACCTCTTATATTTC-----AGATCTGC
                1420
Uce_Oryza_4         TTTCCGAATTTTATTAGTAGTTGCGATATTATTAATACAGGTCTCGT-----AGCGGCCG 483
UBI9_Saccharum      GTCAAGTGTCATCTCCTGACGTGGACTGGAGCTACGGTGAGCCAACCG----AGATGTTA 849
Enolase_Zea         TACAAATTTACAATAAATAAAGTTCCTAGATTTTGAACGAAACCAGC-----AGAGCGCA 519
Actin-2_Zea         GCCGGGATGCGCGTATAAAAACCGGCGAAACCCTTGGCTCTCCTCATT----CGGCCTAT 515
Uce_Oryza_2         ACAACCAAACACCTGTCAAATTTGCCTAACCTTAGGCGTGGCAAACTG----TGGCAAAG
                1477
UceS8.3             AGAAAGAAATGGATAAGGGTGTCATTTGGTGTGGGCATATATCCAAC-----CAAAAAGG 859
A-Tubulin_Coffea_2  AGACATAGGCGGGACCCCAGCTCTGCCGACCTGGAAATACCCTCCTCA----TATACCAT 752
35Sd_AMV            CAACCACGTCTTCAAAGCAAGTGGATTGATGTGATATCTCCACTGACGTAAGGGATGACG 549

Arabidopsis         CAGTGATC--CCAGATTCT-ACACTCT-AAATTTGTTGGTCTAA-GAA----------C 632
Uce_Oryza_3         CACCACCA--CCA---CCA-CCACTCC-A---CCGATCGGCGAGA-GCG---------C 357
Gos-2_Zea           TAATATTT--TTGTCTCTATAGATACT-ACGTGCAACAGTATAA-TCAA--------CCT 450
Uce_Oryza_1         CCCCCTTT--CCGTTCCTTTCTTTCCT-TCTCGCGTTTGCGTGG-TGGGGACGGACTCCC 716
A-Tubulin_Coffea_1  TGTTTCTC--TCATTTTTGTTCAAGGA-AATGATTCATCTTTGG-TTTGATTTTGGGTGT
                1476
Uce_Oryza_4         CGTCTCCT--CCTCCCTTATATAAAGG-CAGCGTTTCTGCAAGT-TATTACCCAATCTAC 539
UBI9_Saccharum      TGCGCCGG--TTCCAATGATGGAGAGG-GGATGGGTGAGAGTGG-CGGAGCCTACATTGT 905
Enolase_Zea         CACCGTCC--TTG-CCCCACGGAACAA-GAAAAATGGAATATGC-TCCCGCAGCCCTCGT 574
Actin-2_Zea         CACAACCG--CTT-ACTCTCGTGCGCT-CTCCGTGGGAGCGAGG-ACCCGCGGCCG -GC 568
Uce_Oryza_2         TGTGGCTT--ACAACCAAACACACCCTTAGATAATAAAATGTGG-TCCAAAGCGTAATTC
                1534
UceS8.3             GACATTTT---GCGGGTATTTGTGAGTGTGTGAGAGAGAGAGCGAGCAGTTTCAGACACAG 917
A-Tubulin_Coffea_2  TACTAGTTAGTAGTCACCACTGCTACTGCTTCAGTTCCTTTTATCACTTGCTTTACATGA 812
35Sd_AMV            CACAATCCCACTATCCTTCGCAAGACCCTTCCTCTATATAAGGAAGTTCATTTCATTTGG 609

Arabidopsis         A-GTGAAATTGTTGTTTCAGT--GATCCCAG----------------------------- 660
Uce_Oryza_3         G-GGGAGATCGTT-CGACGGC-GGCAAGATGC---------------------------- 386
Gos-2_Zea           T-ATAATATTTTTGTCTCTATAGATACTACG----------------------------- 480
Uce_Oryza_1         C-AAACCGCCTCTCCCTCTCTTTATTTGTCTATATTCTCACTGGGCCCCACCCACCGCAC 775
A-Tubulin_Coffea_1  T-GTGGAATAGCCTGATGGACAAATGCCGAGCGACCACACCGTCGGAGGCGGAGACGACG
                1535
Uce_Oryza_4         ACGAGAGAGAGATCGTTCGACGCATATAGAGAGAGAGAGAGATAGGGCAAGATGC----- 594
UBI9_Saccharum      GCGCATACCGTGTGGGCCGCGGGATAAATACCTCAAGAAGGAAGCGTTGTGGCCTCACCT 965
Enolase_Zea         GGAAACCAAGGGCGGACCTTCCCCTC---------------------------------- 600
Actin-2_Zea         GGCAGCGGCAGCTTCTCCTAGATCTCCGGCATCATCAGTGGATCC--------------- 613
Uce_Oryza_2         ACTAAAAAAAAAT-CAACGAGACGTGTACCAAACGGAGAGCAACGGCATCTTCTCGAAAT
                1593
UceS8.3             AGAGAGGGGTTTGGGATTGGAGGGATTGACGCTGCGTCTCTTCCTCTTCTCTTTCGATCC 977
A-Tubulin_Coffea_2  ATTAAGTCGATGCTCTTCCTTGAATAACTAGCGATTAGTTTCGTGGTGACCTATCTAGCC 872
35Sd_AMV            AGAGGAGATCTTTTTATTTTTAATTTTCTTTCAAATACTTCCAC---------------- 653

Arabidopsis         ------------------------------------------------------------
Uce_Oryza_3         ------------------------------------------------------------
Gos-2_Zea           ------------------------------------------------------------
Uce_Oryza_1         CCCTGGGCCCACTCACGAGTCCCCCCCTCCCGACCT------------------- 811
A-Tubulin_Coffea_1  CTTTCAACACCTTCTTCAGCGAAACCGGAGCCGGCAAACACGTTCCTCGTGCCGTGTTCG
                1595
Uce_Oryza_4         ------------------------------------------------------------
UBI9_Saccharum      CCAAGAGTTTGTCGATGGAGCCCTTGCGCATATCCTGAACATGTCCAAGGCTCTGGGAGA
                1025
Enolase_Zea         ------------------------------------------------------------
Actin-2_Zea         ------------------------------------------------------------
Uce_Oryza_2         TTCCCAACCGCTGGCTGGCCCGCCTCGTCTTCCCGGAAACCGCGGTGGTTTCAGCGTGGC
                1653
UceS8.3             ATCCCTCATTCCTAATCCTCCAATCCAACCACCTCAGCCCCACACTCACATATACACATG
                1037
A-Tubulin_Coffea_2  ATTTTTCTGTTTGGGTGGCATCAATCCTGAACACAGAAAGCTGCAAG------------ 919
35Sd_AMV            --------                                            -------
```

FIGURE 4G

```
Arabidopsis               ------------------------------------------------------------
Uce_Oryza_3               ------------------------------------------------------------
Gos-2_Zea                 ------------------------------------------------------------
Uce_Oryza_1               ------------------------------------------------------------
A-Tubulin_Coffea_1        TCGATCTGGAGCCCACTGTCATCGATGAAGTCCGAACCGGCACCTACCGCCAACTCTTCC
1655
Uce_Oryza_4               ------------------------------------------------------------
UBI9_Saccharum            GCAGGTTGGAAATGGGAGGCCAGTACTGCCTTACGTGATACATGGGCACTATGCC-----
1080
Enolase_Zea               ------------------------------------------------------------
Actin-2_Zea               ------------------------------------------------------------
Uce_Oryza_2               GGATTCTCCAAGCAGACGGAGACGTCACGGCACGGACTCCTCCCACCACCCAACCGCCA-
1712
UceS8.3                   TCTCTCTCTATTTCCCTTTTCACTTTCACTTTCATTTCTAGGGTTCCGTTCTGATGGCTC
1097
A-Tubulin_Coffea_2        ------------------------------------------------------------
35Sd_AMV                  ------------------------------------------------------------

Arabidopsis               ------------------------------------------------------------
Uce_Oryza_3               ------------------------------------------------------------
Gos-2_Zea                 ------------------------------------------------------------
Uce_Oryza_1               ------------------------------------------------------------
A-Tubulin_Coffea_1        ACCCTGAGCAGCTCAT--------------------------------------------
1671
Uce_Oryza_4               ------------------------------------------------------------
UBI9_Saccharum            ------------------------------------------------------------
Enolase_Zea               ------------------------------------------------------------
Actin-2_Zea               ------------------------------------------------------------
Uce_Oryza_2               ------------------------------------------------------------
UceS8.3                   TTTCCCTTTCAGATCTGAACGCGTATCGTCCCTCCTATGGCTTCAAAGCGCATCCTCAAG
1157
A-Tubulin_Coffea_2        ------------------------------------------------------------
35Sd_AMV                  ------------------------------------------------------------

Arabidopsis               ---------------
Uce_Oryza_3               ---------------
Gos-2_Zea                 ---------------
Uce_Oryza_1               ---------------
A-Tubulin_Coffea_1        ---------------
Uce_Oryza_4               ---------------
UBI9_Saccharum            ---------------
Enolase_Zea               ---------------
Act
Uce
Uce
A-T
35S
```

FIGURE 4H

COMPOSITIONS AND METHODS FOR MODIFYING GENE EXPRESSION USING THE PROMOTER OF UBIQUITIN CONJUGATING PROTEIN CODING GENE OF SOYBEAN PLANTS

RELATED APPLICATIONS

This application is a continuation of U.S. application Ser. No. 12/017,312 filed Jan. 21, 2008, now abandoned which claims priority to application PI 0701172-5 filed in Brazil on Feb. 5, 2007, the contents of which are incorporated herein by reference in their entireties.

REFERENCE TO SEQUENCE LISTING

The present application is being filed along with a Sequence Listing in electronic format. The Sequence Listing is provided as a file entitled CASCH2.002SUBSEQ.TXT, created May 28, 2009, which is approximately 3.2 KB in size. The information in the electronic format of the Sequence Listing is incorporated herein by reference in its entirety.

FIELD OF THE INVENTION

The present invention relates to a novel promoter for gene expression in plants. More specifically, the invention refers to regulatory sequences of polynucleotides isolated from soybean plants capable of initiating and activating the transcription of polynucleotides, and the use of these regulatory sequences for modifying the transcription of endogenous and/or heterologous polynucleotides and the production of polypeptides. The invention also describes DNA constructs that contain the promoter of ubiquitin conjugating protein coding gene of soybean plants operably linked to a heterologous and/or endogenous gene. Furthermore, the invention concerns the use of these constructs in the form of expression vectors, recombinant vectors and in plants, plant cells or transgenic protoplasts. The invention also describes a method using such constructs containing the promoter of ubiquitin conjugating protein coding gene of soybean plants for the production of plants, plant cells or transgenic protoplasts.

BACKGROUND OF THE INVENTION

The expression of a gene is regulated, at least partly, by cellular processes involved in transcription. During transcription, a single strand RNA, complementary to DNA sequence is formed by the action of RNA polymerases. The start of transcription in eukaryotic cells is regulated by complex interaction between cis-active DNA motives located within the gene to be transcribed and trans-active protein factors. Among cis-active regulatory regions are the DNA sequences known as promoters, to which RNA polymerase primarily binds, directly or indirectly. For the purpose of the present invention, the term "promoter" refers to specific DNA sequences—usually "upstream" (5') of the coding region of a structural gene—that controls the expression of this coding region due to its ability to provide a recognition site for the RNA polymerase and/or other necessary factors for initiating transcription, as well as defining the correct location for gene transcription.

Typically, a promoter sequence comprises a "TATA box" and an upstream activating region. This TATA box is responsible for defining the location of transcription start site, normally approximately 25 base pairs towards the start of the coding sequence of the gene (3').

These promoters are basically divided into inducible and non-inducible (also termed constitutive) types. An inducible promoter is one capable of activating (directly or indirectly) the transcription of one or more DNA sequences or genes in response to a determined inducer. When there is no inducer, the DNA sequences or genes are not transcribed. This inducer may be a chemical component (described in patent document WO9519443, for example), some form of stress of physiological origin (such as in the case of wounds, described in patent document U.S. Pat. No. 6,677,505, for example), or an endogenous compound generated in response to changes in plant development.

There are many tissue-specific promoters described in plants, such as the case of specific expression in seed (WO8903887), tubercle (as mentioned in patent application US20030175783, Keil et al., 1989 EMBO J. 8: 1323:1330), leaves (as mentioned in patent application US20030175783, Hudspeth et al., 1989 Plant Mol. Biol. 12:579-589), fruit (Edwards & Coruzzi (1990) Annu. Rev. Genet. 24, 275 to 303 and U.S. Pat. No. 5,753,475), stem (as mentioned in patent application US20030175783, Keller et al., 1988 EMBO J. 7: 3625-3633), vascular tissue (as mentioned in patent application US20030175783, Peleman et al., 1989 Gene 84: 359-369 and Schmtilling et al. (1989) Plant Cell 1, 665-670), root (US20060143735 as mentioned in patent application US20030175783, Keller et al., 1989 Genes Devel. 3:1639-1646), stamen (WO8910396, WO9213956), specific promoters for the dehiscence zone (WO9713865) and meristem (Ito et al. (1994) Plant Molecular Biology, 24, 863 to 878).

On the other hand, constitutive promoters are capable of conducting the expression of DNA sequences throughout the development of a plant and lack specificity as to the site of sequence expression. Therefore, expression occurs in a large variety of cells and tissues of the plant. Despite this, the term "constitutive" does not imply that the sequence is expressed in similar levels in all plant cells.

Recombination techniques make it possible to trigger the transcription start site of a nucleotide sequence of interest—such as a heterologous or non-natural sequence—in a plant host cell.

The promoters that drive constitutive expression of the genes under their control may be used, for example, to select transformed plant cells, to express a selection marker gene in transgenic plants, in generating plant cells resistant to antibiotics or for creating herbicide or insecticide tolerant plants and pathogen stress resistant plants, since the products of the genes controlled by these promoters are present in all parts of the plant.

Exogenous genes of agronomic, medical or other interest may be expressed in a variety of plants, for example, to generate heterologous recombinant proteins and for the generation of plants that contain mammal polypeptides. The quantities of expression patterns—both in terms of time and space—of endogenous plant genes may also be advantageously altered with the help of constitutively active promoters.

The first promoters used for the expression of genes in plants were of viral or bacterial origin, for example, bacteria from *Agrobacterium* genus. Both viral and bacterial systems carry advantages in the case of heterologous expression in plants since this character constitutes the basis of their infection mechanisms. Many of these promoters have being widely used for expressing proteins of interest in the production of genetically modified plants.

Apart from *Agrobacterium* T-DNA derived promoters, such as those responsible for synthase of manopine (mas), octopine (ocs) and nopaline (nos), there are also virus derived promoters, with the most commonly used being CaMV35S, which corresponds to the cauliflower mosaic virus 35S promoter fragment. Later, this same promoter had its regulatory region duplicated and fused to an enhancer sequence of the alfalfa mosaic virus, generating a highly efficient recombinant plant promoter for inducing expression of coding sequences associated to it.

Other constitutive promoters of viral origin are, for example, the scrofularia mosaic virus promoter (PI1101063-0), of the badnavirus that infects the Australian banana (U.S. Pat. No. 6,391,639) and the promotor of the sugar-cane baciliform virus (U.S. Pat. No. 6,489,462). However, viral and *Agrobacterium* promoters present problems related to their regulatory capacity and may be particularly unstable and suitable to horizontal gene transfer and gene recombination, which tends to highlight the importance of seeking promoters of plant origin.

Typical constitutive promoters of plants are, for example, the coffee alpha tubulin promoter (U.S. Pat. No. 6,441,273), the *A. thaliana* trehalose 6-phosphate synthase protein promoter (US20020115850), maize actin-2, enolase, Gos-2 and L41 promoters (U.S. Pat. No. 6,670,467), Beta vulgaris V-ATPase promoter (PI0013537-2), *Brassica* hsp80 promoter (PI9300296-3).

Despite that many of these plant promoters demonstrate a strong expression, data for the promoters presented herein basically refers to a qualitative analysis. However, the present invention further presents quantitative data obtained by means of fluorimetric tests that upon analysis demonstrated its high expression capacity.

The promoters described above were aligned with the present invention and showed no significant sequence identity between them. The coffee alpha tubulin promoter obtained the best alignment with an identity of 42.7%. This alignment may be performed using softwares available on the internet, with one being the BLASTN provided on the National Centre for Biotechnology Information/NCBI page: (ncbi.nlm.nih.gov).

The *A. thaliana* trehalose 6-phosphate synthase protein promoter (US20020115850) shows a reduction in activity in root during plant development. The present invention, however, presents high expression throughout plant tissues of transgenic *Arabidopsis* over 3 months, showing that uceS8.3 presents expression capacity in high levels, not only during development stages but also in mature plants. The results obtained with uceS8.3 promoter shows that uceS8.3 has a great technological potential considering that most plants are attacked by insect-pests throughout plant's life.

It is desirable that whenever possible the available promoters enabling expression of selection genes and resistance genes present strong and uniform constitutive activity, when possible, throughout plant tissues or cell types that, furthermore, present even greater activity or are not inhibited under stress conditions.

Even if the above mentioned promoters are considered as being constitutive, time and spatial expression patterns are different, rendering them inappropriate for determined purposes. This makes the search and study for other plant promoters crucial. Furthermore, high expression levels are needed to increase the levels of the protein product of interest required for certain purposes in the generation of genetically modified plants. High protein expression levels help in the generation of plants by presenting commercially important phenotype properties, such as resistance to insect-pests and diseases, environmental stress tolerance (e.g. drought, high temperatures, cold, light intensity, photoperiod and chemicals, amongst others), improved quality (e.g. high fruit yield, extended life cycle, size and colour uniformity, high sugar content, high vitamin A and C and reduced acidity, amongst others).

Promoters may become more effective when isolated from the same species of the transgenic plant generated. The expression of β-glucuronidase (GUS) controlled by rice actin (Act1) promoter in protoplasts of transformed rice was approximately 6 times greater than the expression controlled by the maize constitutive promoter alcohol dehydrogenase (Adh1) (US658701). Therefore, apart from being used as constitutive promoters for various plant species, the present invention advances a promoter having great advantages concerning the production of transgenic soybean plants.

Ubiquitin is one of the more conserved proteins in eukaryotes. One of the physiological functions of ubiquitin is to conjugate with a target protein as a recognition signal for protein degradation. Selective degradation of abnormal proteins is performed on many short lived regulatory proteins, including cell cycle proteins, cellular growth modulators and transcription factors. In more complex organisms, ubiquitin has been encoded by two small gene families termed "polyubiquitin genes" and "ubiquitin fusion genes". Polyubiquitin genes comprise a tandem repetition from head to tail of 228 bp, with each repetition encoding 76 amino acids of an ubiquitin monomer. The number of tandem repetitions indicated varies between genes and within the genomes and between organisms, ranging from 3 in Dictostylium to approximately 50 in *Trypanosoma cruzi*. On the other hand, the ubiquitin fusion gene family encodes a simple repetition fused with one or two polypeptides having 52 or 76-80 amino acids each (Callis et al., "Ubiquitin and Ubiquitin Genes in Higher Plants", Oxford Surveys of Plant Molecular & Cell Biology, (1989), vol. 6, pp. 1-30). Studies of ubiquitin genes in different plants show that ubiquitin genes are expressed in all tissues; however, the differential expression of ubiquitin genes can also be observed in the ubiquitin gene family. Each tandem repetition or ubiquitin gene may be differentially expressed in cells or tissues, and in time.

Ubiquitin gene promoters have demonstrated the ability to conduct the expression of genes—usually GUS or chloranphenicol acetyltransferase (CAT)—in transformed cells or plants. Such promoters have been isolated from *Arabidopsis* (Callis et al., "Ubiquitin Extension Proteins of *A. thaliana*", The Journal of Biological Chemistry (1990), vol. 265, n. 21, pp. 12486-12493); sunflower (Binet et al., "Analysis of a sunflower polyubiquitin promoter by transient expression" (1991) Plant Science, vol 79, pp. 87-94); tobacco (Genschick et al., "Structure and promoter activity of a stress and developmentally regulated polyubiquitin encoding gene of *Nicotiana tabacum*", Gene, (1994) vol. 148, pp.195-202); maize (US20030066108; U.S. Pat. No. 6,020,190; U.S. Pat. No. 5,614,399; U.S. Pat. No. 5,510,474; Christensen et al., "Maize polyubiquitin genes: structure, thermal perturbation of expression and transcript splicing, and promoter activity following transfer to protoplasts by electroporation", Plant Molecular Biology, (1992) vol. 18, pp. 675-689); rice (U.S. Pat. No. 6,528,701); sugar-cane (U.S. Pat. No. 6,706,948); celery (WO2003102198); Pine and eucalyptus (PI0309870-2). These promoters were aligned with the present invention using BLASTN and showed no similarity.

Patent documents US20030066108; U.S. Pat. No. 6,020, 190; U.S. Pat. No. 5,614,399 and U.S. Pat. No. 5,510,474 describe engineered versions of the maize ubiquitin promoter used to increase expression levels compared to the expression levels of the native ubiquitin promoter. The invention reports that the promoter regulates the expression of maize polyubiquitin gene containing 7 tandem repetitions. The expression of this ubiquitin gene proved constitutive at 25° C. and was heat induced at 42° C. This promoter was used successfully to transform monocots other than maize, including wheat, barley and rice. However, the promoter of the present invention proved to be an excellent constitutive promoter and does not undergo any change in expression levels when submitted to different temperatures as well as presenting high expression throughout the plant cycle.

The control of insect-pests is a priority since the culture of soybean is—with a production of over 60 million tons.

The production of genetically modified plants expressing proteins conferring resistance to the plant has been used with great success in insect-pests control. However, it is necessary to control and target the expression of these entomotoxic proteins in order to obtain these plants. Transgenic plants affording adequate protein levels conferring insect resistance to plants depend on the choice of promoters that conduct the expression. The choice of the promoters that conduct expression is very important for obtaining transgenic plants affording adequate protein levels conferring insect resistance to plants. However, there are few effective promoters for expressing soybean plants available on the market at present, and none that demonstrate superior expression efficiency compared to the promoter of the present invention.

SUMMARY OF THE INVENTION

The present invention relates to a description of a new regulatory sequence provided to improve the expression of a nucleotide sequence, such as structural genes, in plants, including monocots and dicots. In accordance with the present invention, a constitutive promoter for soybean plants (Glycine max) termed uceS8.3 is described together with a method for the use of this regulatory polynucleotide region for the modification of endogenous and/or heterologous polynucleotide expression in transgenic plants.

In a first embodiment, the present invention provides a polynucleotide sequence isolated from soybean plants (Glycine max) comprising at least about 40 or 45%, 50 or 55%, 60 or 65%, 70 or 75%, 80 or 85%, 90%, 91%, 92%, 93%, 94%, 95%, 96%, 97%, 98%, or 99%, when compared with SEQ ID NO:1, wherein said polynucleotide has constitutive promoter activity. Additionally the present invention provides sequences that are the complement of said polynucleotide sequence; the reverse complement of said polynucleotide sequence; the reverse of said polynucleotide sequence; and probes and primers corresponding to SEQ ID NO:1.

In another embodiment, the present invention provides chimeric genes comprising sequences having sequence identity at least about 40 or 45%, 50 or 55%, 60 or 65%, 70 or 75%, 80 or 85%, 90%, 91%, 92%, 93%, 94%, 95%, 96%, 97%, 98%, or 99%, when compared with SEQ ID NO:1, optionally linked to expression enhancer or promoter sequences of interest; operably linked to a polynucleotide sequences of interest. In addition, cells and organisms may comprise said chimeric genes.

In a related embodiment, the present invention provides recombinant vectors incorporating a promoter sequence in 5'-3' sense for the polynucleotide of the present invention, a polynucleotide to be transcribed and a gene termination sequence. The polynucleotide to be transcribed may either incorporate the open reading frame of a polynucleotide encoding a polypeptide of interest, or may be a non-translated, or non-encoding region of a polynucleotide of interest. The open reading frame may be oriented in "sense" or "antisense" direction. Preferably, the gene termination sequence is functional in a host plant. More preferably, the gene terminator sequence is that of the gene of interest, but may be others described in the state of the art (see Benjamin Lewin, Genes VIII, chapter 9) such as nopaline synthase terminator of *A. tumefasciens*. The recombinant vectors may also include a marker for identifying the transformed cells.

In yet another embodiment, cells of transgenic plants comprising the recombinant vector of the present invention are provided, together with organisms, such as plants, incorporating these transgenic cells, and the fruits, seeds and other products, derivates, or progeny of these plants. The propagula of the inventive transgenic plants are included in the present invention.

Another embodiment of the present invention provides a method for modifying the expression of genes in an organism, such as a plant, including stable incorporation in the genome of the organism containing the recombinant vector of the present invention.

A further embodiment of the present invention provides a method for producing a transformed organism, such as a plant, through the expression of a modified polypeptide. This method consists in transforming a plant cell with the recombinant vector of the present invention in order to provide a transgenic cell under conditions conducive to the regeneration and growth of the mature plant.

Yet another embodiment of the present invention provides a method for identifying a gene responsible for a certain function or desired phenotype. The method comprises: 1) transformation of a plant cell containing a recombinant vector comprising a polynucleotide promoter sequence of the present invention operationally linked to a polynucleotide to be tested, 2) plant cell culture under conditions capable of inducting regeneration and growth of mature plant in a manner as to produce a transgenic plant, and, 3) comparing transgenic plants phenotype with those of non-transformed plants, or of wild plants.

All the above mentioned embodiments and others of the present invention as well as the means of obtaining these shall be made evident and the invention may be better understood referring to the "Detailed Description of the Invention".

BRIEF DESCRIPTION OF THE FIGURES

FIG. 4A-H—Alignment between the different constitutive promoters and the promoter of the present invention (uceS8.3).

DETAILED DESCRIPTION OF THE INVENTION

Figure 1:
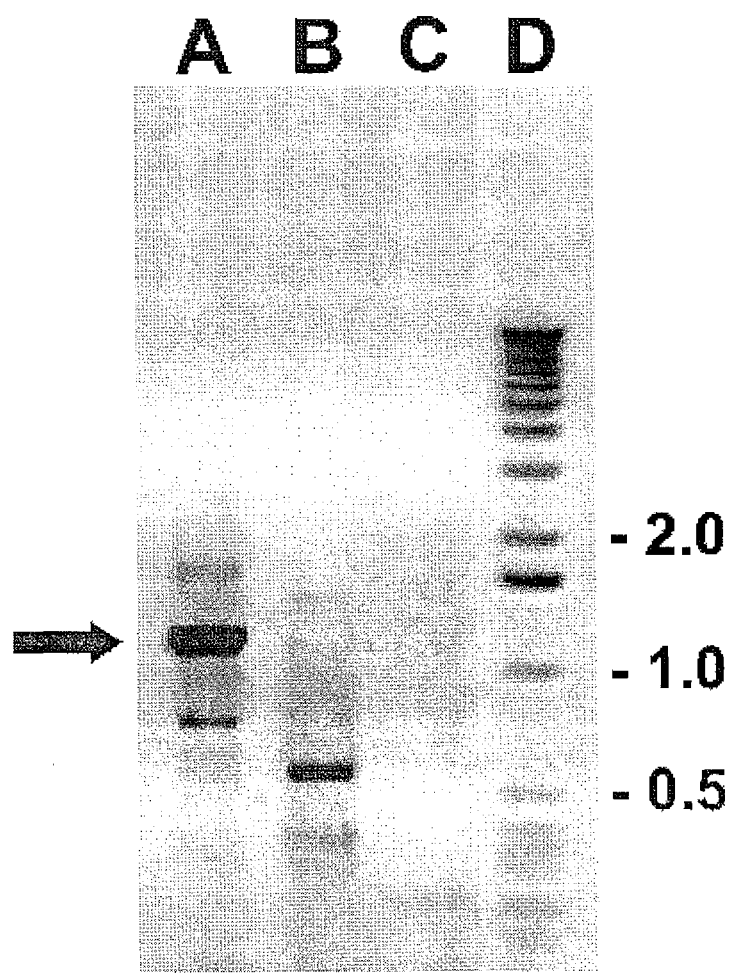
FIG. 1—Agarose gel showing the amplification product with random primer AD3 producing a fragment of approximately 1.2 kb. (A) reaction with primers AD3 and uce2; (B) control reaction just with primer AD3; (C) control reaction just with primer uce2; (D) molecular mass marker (1 kb DNA-ladder, Gibco-BRL) indicated in kb. The arrow points out the potentially positive amplified fragment of approximately 1.2 kb.

In the context of this description, several terms are used and it therefore seems appropriate to provide the following definitions for these:

The term "chimeric gene" refers to a gene incorporating a promoter and an encoding region having different origins. In the case of the present invention, the chimeric gene includes the polynucleotide of the present invention linking the encoding regions of endogenous and/or exogenous genes.

The term "consensus sequence" refers to an artificial sequence in which the base of each position represents the base more frequently found in the actual sequence when comparing to different alleles, genes or organisms sequences.

The term "promoter" refers to a DNA portion that is upstream to the coding region and contains RNA polymerase II binding sites to initiate the DNA transcription.

The term "expression" refers to the transcription or translation of a structural, endogenous or heterologous gene.

The term "GC box" refers to a common element in the promoter that may increase promoter activity.

The term "TATA box" refers to a promoter element, located approximately 30 bases upstream the transcription initiation site. The TATA box is associated to transcription factors in general, including RNA polymerase II.

The term "gene" refers to a physical and functional hereditary unit represented by a DNA segment that encodes a functional protein or RNA molecule.

The term "endogenous gene" refers to a gene specific to the cell or organism.

The term "heterologous gene" refers to a gene isolated from a donor organism and recombined in the transformed host organism. It is a gene that is not specific to the cell or organism.

The term "reporter gene" refers to an encoding unit having a readily tested product, for example, CAT, GUS, GAL, LUC and GFP genes. Expression of a reporter gene may be used to test the function of a promoter linked to this reporter gene.

The term "propagulum" refers to any part of a plant that may be used for the reproduction or propagation, whether sexual or asexual, including plant cuttings.

The term "sense" means that the sequence of the polynucleotide is in the same 5'-3' orientation in relation to the promoter.

The term "antisense" means that the sequence of the polynucleotide is in the opposite orientation in relation to the 5'-3' promoter orientation.

The term "x-mer"—when used as a reference for the specific value of "x" herein—refers to a sequence incorporating at least a specific number ("x") of polynucleotide residues identified as SEQ ID NO:1. In accordance with the preferred embodiments, the value of x is preferably at least 20, more preferably at least 40, even more preferably at least 60 and most preferably at least 80. Thus, the polynucleotide of the present invention include a polynucleotide of 20 mer, 40 mer, 60 mer, 80 mer, 100 mer, 120 mer, 150 mer, 180 mer, 220 mer, 250 mer, 300 mer, 400 mer, 500 mer or 600 mer identified as SEQ ID NO:1 and variants thereof.

The term "polynucleotide(s)" refers to a single or double strand polymer with deoxyribonucleotide or ribonucleotide bases and includes corresponding RNA and DNA molecules, including HnRNA and mRNA molecules, both sense and antisense strands, and incorporates cDNA, genomic DNA and recombinant DNA, as well as completely or partially synthesised polynucleotides. A HnRNA molecule contains introns and corresponds to a DNA molecule generally in a one to one mode. A mRNA molecule corresponds to a DNA and HnRNA molecule from which all introns were excised. A polynucleotide may consist of a complete gene, or any portion thereof. The operational antisense polynucleotides may incorporate a fragment of the corresponding polynucleotide, and the definition for "polynucleotide" thus includes all of these operational antisense fragments. The antisense polynucleotides and techniques involving antisense polynucleotides are well known in the state of the art. (J. Sambrook; E. F. Fritsh and T. Maniatis—Molecular cloning. A laboratory manual, $2^{nd}$ Ed., Cold Spring Harbor Laboratory Press, 1989.).

The polynucleotides described in the present invention are preferably approximately 80% pure, more preferably 90% pure, and most preferably at least 99% pure.

The term "oligonucleotide" refers to a relatively short segment of a polynucleotide sequence, generally incorporating between 6 and 60 nucleotides. These oligonucleotides may be used as probes or primers, whereby the probes may be used to serve as hybridisation tests and primers are used in DNA amplification by PCR.

The term "probe" refers to an oligonucleotide, polynucleotide or nucleic acid, being RNA or DNA, occurring naturally such as a purified product of restriction enzyme digestion or being synthetically produced, capable of specifically annealing or hybridising with a nucleic acid containing complementary sequences to the probe. A probe may also be single chain or double chain. The exact length of the probe will depend on many factors, including temperature, probe origin and use of the method. For example, an oligonucleotide probe will typically contain between 15-25 or more nucleotides depending on the complexity of the target sequence, although it may contain fewer nucleotides. The probes herein are selected in order to complement the different chains of a particular nucleic acid sequence. This means that a probe may be sufficiently complementary to be able to "hybridise specifically" or for annealing with their respective target chains under a series of pre-determined conditions. Consequently, the probe sequence does not necessarily exactly reflect the complementary target sequence. For example, a fragment of non-complementary nucleotide may be linked to the 5' or 3' end of the probe, with the remaining probe sequence being complementary to the target chain. Alternatively, non-complementary bases or long sequences may be interspersed within the probe if it is sufficiently complementary with the sequence of the target nucleic acid to specifically anneal with it.

The term "primer" refers to an oligonucleotide, being RNA or DNA, single chain or double chain, derived from a biological system, generated by digestion with restriction enzymes or being synthetically produced, that, when placed in an appropriate environment, is capable of acting functionally as the primer for the synthesis of nucleic acid depending on the template. When in presence of an appropriate nucleic acid template, adequate nucleoside triphosphate precursors of nucleic acids, a polymerase enzyme, adequate cofactors and suitable conditions such as adequate temperatures and pH values, the primer may be extended at its 3' terminal through the addition of nucleotides by polymerase activity or some similar activity to produce a first extension of the product. The primer may vary in length depending on particular conditions and requirements for use. For example, when used as a diagnostic, the oligonucleotide 'primer' typically has a length of 15-25 or more nucleotides. The 'primer' must have sufficient complementarity with the intended template to initiate extension synthesis of the product. This does not mean that the 'primer' sequence must precisely complement the intended template. For example, a non-complementary nucleotide sequence may be linked to the 5' terminal of a complementary 'primer'. Alternatively, non-complementary bases may be interspersed within the oligonucleotide sequence of the 'primer', provided the 'primer' has sufficient complementarity with the desired template chain sequence to functionally form a template-primer complex for the extension synthesis of the product.

The term "specifically hybridise" refers to the association of two single chain nucleic acid molecules having sufficiently complementary sequences in order to allow such hybridization under pre-determined conditions commonly described in the state of the art (Handbook: Tecnologia de DNA recombinante. Universidade de Sao Paulo, Chapter 1, 2003) [Recombinant DNA technology. University of Sao Paulo].

More precisely, the term refers to the hybridisation of an oligonicleotide with a substantially complementary sequence containing a single chain RNA molecule or DNA molecule from the present invention. Optimal conditions necessary for specific hybridisation between single chain nucleic acid molecules of varying complementarity are well described in the state-of-the-art (Handbook: Tecnologia de DNA recombinante. Universidade de Sao Paulo, Chapter 4, 2003) [Recombinant DNA technology. University of Sao Paulo]. A common formula enabling calculation of the required stringency conditions to obtain hybridization between nucleic acid molecules is provided below (Sambrook et al., Molecular Cloning, A Laboratory Manual, $2^{nd}$ Ed. (1989), Cold Spring Harbor Laboratory Press):

$$T_m = 81.5° C. + 16.6 \text{ Log } [Na+] + 0.41 (\% G+C) - 0.63 (\% \text{ formamide}) - 600/bp \text{ in duplex (probe)}$$

As can be seen from the above formula, using $[Na^+]= [0.368]$ and 50% of formamide, with 42% GC content and an average probe size of 200 bases, $T_m$ shall be 57° C.

Probes or primers are described as corresponding to the polynucleotide of the present invention identified as SEQ ID NO:1 or a variant thereof, when the oligonucleotide probe or primer, or its complement, are contained within the sequence specified as SEQ ID NO:1, or a variant thereof.

The term "oligonucleotide" refers to 'primers' and 'probes' of the present invention, and it is defined as a molecule of nucleic acid incorporating two or more ribo- or deoxyribonucleotides, preferably more than three. The exact size of the oligonucleotides depends on various factors and in the particular purpose and use of the oligonucleotide. Preferred oligonucleotides incorporate 15-50 consecutive complementary base pairs for SEQ ID NO:1. The probes may be easily selected using procedures thoroughly described in the state of the art (Sambrook et al., Molecular Cloning, A Laboratory Manual, $2^{nd}$ Ed. (1989), Cold Spring Harbor Laboratory Press, NY), taking into consideration DNA-DNA hybridization stringency, recombination and melting temperatures ($T_m$), as well as the potential for forming bonds and other factors, all well known in the state of the art.

The terms "complement", "reverse complement" and "reverse sequence" referred to herein are described in the following example: For sequence 5'AGTGAAGT3', the complement is 3'TCACTTCA5', the reverse complement is 3'ACTTCACT5' and the reverse sequence is 5'TGAAGTGA3'.

The term "variant" or "substantially similar" refers to different sequences of amino acids or nucleotides with specifically identified sequences, in which one or more nucleotides or amino acid residues are deleted, substituted or added. The variants may be naturally allelic variants or non-naturally occurring variants. The variant or substantially similar sequences refer to fragments of nucleic acid that may be characterised by the percentage of similarity in their nucleotide sequences with the nucleotide sequences described herein (SEQ ID NO: 1), determined by algorithms commonly used in the state of the art. The preferred fragments of nucleic acid are those whose nucleotide sequence has a sequence identity of around 40 or 45% at least, preferably a sequence identity of around 50 or 55%, more preferably a sequence identity of around 60 or 65%, more preferably a sequence identity of around 70 or 75%, more preferably a sequence identity of around 80 or 85%, and even more preferably a sequence identity of around 90%, 91%, 92%, 93%, 94%, 95%, 96%, 97%, 98% or 99%, when compared to the reference sequence. The percentage identity is determined by aligning the two sequences to be compared, determining the number of identical residues in the aligned portion, dividing this number by the total number of residues in the sequence under study and multiplying the result by 100. This alignment may be performed using software available on the internet, with one being the BLASTN provided on the National Centre for Biotechnology Information/NCBI page: (ncbi.nlm.nih.gov).

The term "vector" refers to a replicon, such as a plasmid, cosmid, bacmid, phage or virus, to which other genetic sequences or elements (whether DNA or RNA) may be linked to be replicated together with the vector. Preferably, the virus derived vector is selected from bacteriophage, vaccinia virus, retrovirus or bovine pappilomavirus. A "recombinant vector" is result of combination of a commercial vector with chimeric genes, or the polynucleotide of the present invention operably linked to an endogenous and/or heterologous polynucleotide of interest that in turn is operably linked to a termination signal sequence. Such vectors may be obtained commercially, and include Clontech Laboratories, Inc. (Palo Alto, Calif.), Stratagene (La Jolla, Calif.), Invitrogen (Carlsbad, Calif.), New England Biolabs (Beverly, Mass.) and Promega (Madison, Wis.). Some examples of vectors used in the present invention—but not limited to these—are the pGEM-T and pCAMBIA1391.

The term "expression enhancer sequences" refers to amplifiers—or "enhancers" as they are more commonly known—that may be located very far from the promoter (either "upstream" or "downstream") and intensify the transcription of any nearby promoter. The gene expression efficiency in a specific tissue depends on the appropriate combination and integration of the enhancers, the promoters and the adjacent sequences.

The first enhancer that stimulated the transcription of eukaryote genes to be discovered was SV40 (present in the Simian Virus 40 genome). Following the discovery of the SV40 enhancer Hundreds of other enhancers were discovered, such as HSV-1, AMV, HPV-16, in other viral genomes in eukaryote cells DNA. (Lodish et al., Biologia celular e molecular. [Molecular and cellular biology] $4^{th}$ Ed. p. 368).

The term "operably linked" means that regulatory sequences necessary for the expression of the encoding sequence are placed in the DNA molecule in appropriate positions in relation to the coding sequence enabling the expression of the coding sequence. This same definition is sometimes applied to the arrangement of encoding sequences and elements controlling the transcription (such as, for example, promoters, "enhancers" and elements or termination sequences) in the expression vector. An exogenous coding region is typically flanked by operably linked regulatory regions that regulate the expression of the exogenous coding region in a transformed cell (which may be a micro-organism, plant or animal). A typical regulatory region operably linked to an exogenous coding region includes a promoter, inasmuch, a nucleic acid fragment that may cause the transcription of exogenous coding regions, positioned in 5' of the exogenous coding region. In the case of the present invention, the regulatory region refers to regions substantially similar to SEQ ID NO: 1. To help enhance transcription of a given polynucleotide, the promoter sequence of the present invention may be linked to other regulatory sequences described above, such as: ATATT (element with strong root expression), AACAAAC and GCCACCTCAT (elements related to specific expression in seeds), CACGTG and CCTACC (both these sequences may be stimulated by a stress factor), amongst others (Ai-Min Wu et al., Isolation of a cotton reversibly glycosylated polypeptide (GhRGP1) promoter and its expression activity in transgenic tobacco, Journal of Plant Physiology 163 (2006) 426-435).

A "termination sequence" is a DNA sequence that indicates the end of transcription. Examples of termination sequences are, but not limited to, the SV40 termination signal, the HSV tk adenylation sequence, the nopaline synthase (NOS) gene termination site of *Agrobacterium tumefasciens*, the octopine synthase gene termination site, the 19S and 35S gene termination site of CaMV, the alcohol dehydrogenase gene termination site of maize, the manopine synthase gene termination site, the beta-phaseolin gene termination site, the ssRUBISCO gene termination site, the sucrose synthase gene termination site, the gene termination site of the Subterranean clover stunt virus (SCSV) that infects Trifolium subterranean, the trpC gene termination site of *Aspergillus nidulans* and others similar.

The present invention provides a regulatory region of isolated polynucleotides that may be used in the manipulation of plant phenotypes, combined with isolated polynucleotides incorporating these regulatory regions. More specifically, the present invention relates to a promoter or regulatory sequence that occurs naturally in soybean plants (Glycine max), responsible for the expression of ubiquitin conjugating protein in this plant species. The soybean promoter isolated from the gene responsible for the expression of ubiquitin conjugating protein was named uceS8.3 (SEQ ID NO:1) in the present invention.

The quantity of polypeptide of specific interest may be increased or reduced through the incorporation of additional copies of genes, or coding sequences, thus encoding the polypeptide operably linked to the promoter sequence of the present invention (SEQ ID NO: 1), within the genome of an organism, such as a plant. Likewise, an increase or reduction in polypeptide quantities may be obtained through transformation of plant with antisense copies of these genes.

The polynucleotide of the present invention was isolated from soybean plants, and more specifically from Glycine max, but it may be synthesised alternatively using conventional synthesis techniques. Specifically, the isolated polynucleotide of the present invention includes the sequence set forth in SEQ ID NO:1; the complement of the sequence set forth in SEQ ID NO:1; the reverse complement of the sequence identified as SEQ ID NO:1; and the reverse sequence of the sequence set forth in SEQ ID NO:1.

Studies of the promoter activity of the present invention are provided in more detail in the examples enclosed with this report. Experimental data obtained with *Arabidopsis* quantifying GUS activity demonstrate that the recombinant vector containing the promoter uceS8.3 demonstrates greater GUS activity when compared to CaMVd35S promoter.

The polynucleotide of the present invention may be identified in genomic DNA sequences of plants, for which genome sequence information is available to the public or isolated from several polynucleotide libraries, or may be synthesised using known state-of-the-art techniques (Sambrook et al., "Molecular Cloning, a laboratory manual", CSHL Press, Cold Spring Harbor, N.Y., 1989). The polynucleotide, for example, may be synthesised using automated oligonucleotide synthesizers (i.e. the Beckman DNA OLIGO 1000M synthesiser) so as to obtain polynucleotide fragments of up to 50 or more nucleotides. A multitude of these polynucleotide fragments may then be linked using known state-of-the-art standard DNA manipulation techniques (Sambrook et al., "Molecular Cloning, a laboratory manual", CSHL Press, Cold Spring Harbor, N.Y., 1989). A conventional and exemplary polynucleotide synthesis technique involves the synthesis of a single-stranded polynucleotide segment, containing, for example, 80 nucleotides bases followed by the single-stranded polynucleotide segment with another segment of 85 complementary bases synthesised to produce an 'overhang' of 5 nucleotides. The subsequent segment may then be synthesized in a similar manner, with an 'overhang' of 5 nucleotides from the opposite strand. The "adhesive" overhangs, also known as cohesive ends, ensure an appropriate bond when both portions are hybridised. In this manner, the polynucleotide of this invention may be completely synthesized in vitro.

As noted above, the promoter sequence of the present invention may be used in recombinant and/or expression vectors for triggering transcription and/or expression of a polynucleotide of interest. This polynucleotide of interest may be endogenous or heterologous to an organism, such as, for example, a plant, to be transformed. The recombinant and/or expression vectors of the present invention may thus be used to modulate the levels of transcription and/or expression of a polynucleotide, for example, a wild plant gene, or it may be used to provide the transcription and/or expression of a DNA sequence not found in a wild plant, including, for example, a gene that encodes a reporter gene such as GUS.

In some forms of the present invention, the polynucleotide of interest incorporates an open reading frame that encodes the polypeptide of interest. The open reading frame is inserted in the vector in a sense orientation and a transformation using this type of genetic construct will generally result in selected polypeptide over-expression. The polypeptide of interest to be regulated by the promoter of the present invention may be inserted into vector in sense orientation, antisense orientation or even in both. A transformation with a recombinant and/or expression vector containing the promoter of the present invention regulating the expression of the polynucleotide of interest in an antisense orientation or in both orientation (sense and antisense) will generally result in reduced expression of the polypeptide of interest.

The polynucleotide of interest, as an encoding sequence, is operably linked to the polynucleotide promoter sequence of the present invention in a manner that a host cell is capable of transcribing a RNA activated by the promoter sequence linked to the polynucleotide of interest. The polynucleotide promoter sequence is generally located at the 5' extremity of the polynucleotide to be transcribed. The use of a constitutive promoter such as the promoter sequence for the ubiquitin conjugating protein of *G. max* set forth in SEQ ID NO:1 will affect the transcription of polynucleotide of interest in all parts of the transformed plant.

The recombinant or expression vector of the present invention may also contain a selection marker efficient in cells of the organism, such as a plant, to allow the detection of transformed cells containing the inventive recombinant vector. These markers, that are well known, typically confer resistance to one or more toxins. An example of this marker is the nptII gene, whose expression results in resistance to kanamycin or neomycin, antibiotics that are normally toxic for plant cells in moderate concentrations. The transformed cells may thus be identified by their ability to grow in medium containing the antibiotics at issue. Other selection markers that may be used to construct recombinant and/or expression vectors containing the polynucleotide of the present invention may be, but not are limited to the hpt gene, that confers resistance to the antibiotic hygromycin, the gene manA and the gene bar.

The system using the manA gene (that encodes the PMI enzyme—phosphomannose isomerase) of *Escherichia coli* (Miles & Guest, 1984 Complete nucleotide sequence of the fumarase gene fumA, of *E. coli*, Nucleic Acids Res. 1984 Apr. 25; 12(8): 3631-3642) having mannose as selective agent is one of the new systems advanced as alternatives to the first two described above (Joersbo et al., 1998; Parameters interacting with mannose selection employed for the production of transgenic sugar beet, Physiologia Plantarum Volume 105, Issue 1, Page 109. January 1999 doi:10.1034/j.1399-3054.1999.105117.x). Plant species that do not metabolise mannose suffer severe growth inhibition when the latter is the sole source of carbon provided in the culture medium. The adverse and inhibitory effects resulting from the use of mannose are the consequence of accumulated mannose-6-phosphate which is a product of the mannose phosphorylation by a hexokinase. PMI promotes the interconversion of mannose-6-phosphate and fructose-6-phosphate thus allowing that the former be catabolyzed in the glycolytic pathway (Ferguson & Street, 1958. Analise de sistemas gene marcador/agente seletivo alternativos para selecao positiva de embriões somaticos transgenicos de mamoeiro. [Analysis of alternative gene marker/selective agent systems for positive selection of somatic transgenic embryos of Papaya plants] *Rev. Bras. Fisiol. Veg.*, 2001, vol. 13, n.3, p.365-372. ISSN 0103-3131.

Malca et al., 1967 Advances in the selection of transgenic plants using non-antibiotic marker genes. Physiologia Plantarum Volume 111, Issue 3, Page 269. March 2001 doi: 10.1034/j.1399-3054.2001.1110301.x).

The bar gene (that encodes the PAT enzyme—phosphinothricin-N-acetyltransferase) of *Streptomyces hygroscopicus* (Murakani et al., 1986—The bialaphos biosynthetic genes of *Streptomyces hygroscopicus*: molecular cloning and characterization of the gene cluster. Molecular and General Genetics. 205: 42-50, 1986.), having gluphosinate ammonium (PPT) as selective agent is one of the herbicide tolerant gene types most widely used in genetic engineering for developing plant GMOs. PAT inactivates herbicides that contain PPT as active component through the detoxification of the latter. This detoxification is the result of the acetylation of the free amine group present in PPT and renders the latter incapable of competing in an inhibitory manner with glutamine synthase (GS). This allows the removal of toxic ammonia from plant cells through the conversion of glutamate into glutamine, with this reaction being catalysed by GS (Lindsey, 1992. Molecular cloning of ICAM-3, a third ligand for LFA-1, constitutively expressed on resting leukocytes *Nature* 360, 481-484 (3 Dec. 1992); doi:10.1038/360481a0).

Alternatively, the presence of the desired construct in transformed cells may be determined by other methods known in the state-of-the-art (Sambrook et al., "Molecular Cloning, a laboratory manual", CSHL Press, Cold Spring Harbor, N.Y., 1989), such as Southern and PCR.

The techniques to link the components of inventive recombinant or expression vectors in an operational manner are well known in the state-of-the-art and include the use of synthetic ligands containing one or more restriction endonuclease sites such as that described, for example, by Sambrook et al., ("Molecular Cloning, a laboratory manual", CSHL Press, Cold Spring Harbor, N.Y., 1989). Chimeric genes of the present invention may be linked to a vector having at least one replication system, such as, for example, *E. coli*, and thus, after each manipulation, the resulted constructs may be cloned and sequenced.

Recombinant and/or expression vectors of the present invention may be used to transform a variety of organisms including, but not limited to, plants. The plants that may be transformed using the recombinant and/or expression vectors of the present invention include monocot angiospermae (i.e. gramineae, maize, corn, oats, wheat and barley . . . ), dicot angiospermae (i.e. *Arabidopsis*, tobacco, leguminosae, alfalfa, eucalyptus and maples . . . ) and gimnospermae (i.e. pine, White Spruce and Larch). The plant transformation protocols are well known in the state-of-the-art (Manual de transformação genética de plantas. [Genetic Plant Transformation Manual]. Brasilia: EMBRAPA-SPI/EMBRAPA-CENARGEM, Chapters 2 and 3, 1998). In a preferred embodiment, the recombinant and/or expression vectors are used to transform dicot plants. Preferably, the plant is selected from the Malvaceae family, more preferably of the species Glycine max. Other plants may be transformed in a useful manner with the recombinant and/or expression vector of the present invention, including, but not limited to: *Anacardium, Anona, Arachis, Artocarpus, Asparagus, Atropa, Avena, Brassica, Carica, Citrus, Citrullus, Capsicum, Carthamus, Cocos, Coffea, Cucumis, Cucurbita, Daucus, Elaeis, Fragaria, Glycine, Gossypium, Helianthus, Heterocallis, Hordeum, Hyoseyamus, Lactuca, Linum, Lupinus, Lycopersicon, Malus, Manihot, Majorana, Medicago, Nicotiana, Olea, Oryza, Panieum, Pannesetum, Passiflora, Persea, Phaseolus, Pistachia, Pisum, Pyrus, Prunus, Psidium, Raphanus, Ricinus, Secale,*

*Senecio, Sinapis, Solanum, Sorghum, Theobromus, Trigonella, Triticum, Vicia, Vitis, Vigna* and *Zea*.

The transcription termination signal and the polyadenylation region of the present invention include, but are not limited to, the SV40 termination signal, the HSV tk adenylation site, the nopaline synthase (nos) gene termination signal of *A. tumefasciens*, the termination signal of gene RNA 35S of CaMV, the termination signal of the virus attacking Trifo/ium subterranean (SCSV), the termination signal of gene trpC of *Aspergillus nidulans*, and others similar. Preferably, the gene termination used in the present invention is the gene termination that encodes the ubiquitin conjugating protein of soybean.

The recombinant and/or expression vectors of the present invention may be introduced into the desired host plant genome by a variety of conventional techniques. For example, *A. tumefasciens* mediated introduction; electroporation; protoplast fusion; injection in reproductive organs, injection in immature embryos; microinjection of plant cell protoplasts; use of ballistic methods, such as DNA coated particle bombardment, amongst others. The choice of technique will depend on plant type to be transformed. For example, dicot plants and some monocots and gymnospermae may be transformed using *Agrobacterium* Ti plasmid technology. The recombinant and/or expression vectors may be combined with appropriate T-DNA flanking regions and introduced into the conventional *A. tumefasciens* host vector. The virulence factor of the *A. tumefasciens* host will conduct the insertion of the genic constructs and adjacent marker into the DNA of the plant cell when the cell is infected by the bacteria. *A. tumefasciens* mediated transformation techniques, including disarmament and the use of binary vectors, are well described in the scientific literature (such as mentioned in patent application US 20020152501, Horsch et al. Science 233:496-498, 1984; and Fraley et al. Proc. Natl. Acad. Sci. USA 80:4803, 1983).

Microinjection techniques are well known in the state-of-the-art and well described in the scientific literature and patent documents. The introduction of recombinant and/or expression vectors using polyethylene glycol precipitations is described by Paszkowski et al. (Embo J. 3:2717-2722, 1984, as mentioned in patent application US20020152501). Electroporation techniques are described in From et al. Proc. Natl. Acad. Sci. USA 82:5824, 1985 (as mentioned in patent application US20020152501). Ballistic transformation techniques are described in Klein et al. Nature 327:70-73, 1987 (as mentioned in patent application US20020152501). The introduction of recombinant and/or expression vectors of the present invention may be done in tissues, such as leaf tissues, dissociated cells, protoplasts, seeds, embryos, meristemic regions, cotyledons, hypocotyledons and others.

Preferably, the present invention uses transformation by *A. tumefasciens* mediated introduction. In principle, the preferred method for transformation containing promoters of the present invention is through transformation by *Agrobacterium tumefasciens* mediated introduction using *A. thaliana* as model plant (Clough et al., "Floral dip: a simplified method for *Agrobacterium*-mediated transformation of *A. thaliana*", Plant J. 1998 December;16(6):735-43.). However, other transformation methods may be used to insert recombinant and/or expression vectors of the present invention, such as bioballistics, that consists of a direct DNA transformation technique using micro-projectiles propelled at high speeds to implant DNA in cells which is extremely efficient for transforming soybean (Mccabe et al., Stable transformation of soybean (Glycine max) by particle acceleration. Biotechonoly, v.6, p.923-926,1988).

Once the cells have been transformed, by any of the techniques mentioned above, the cells with the recombinant and/or expression vectors of the present invention incorporated within their genome may be selected by means of a selection marker, such as a kanamynin resistant marker. The cells of the transformed plants may then be cultivated to regenerate an entire plant possessing the transformed genotype and, finally, the desired phenotype. Such regeneration techniques rely on the manipulation of certain phytohormones in tissue culture growth media, typically containing a biocide and/or herbicide marker that must be introduced together with the intended nucleotide sequence. Regeneration of plants from the culture of protoplasts is described in Evans et al. (Protoplasts Isolation and Culture, Handbook of Plant Cell Culture, pp. 124-176, MacMillilan Publishing Company, New York, 1983; and Binding, Regeneration of Plants, Plant Protoplasts, pp. 21-73, CRC Press, Boca Raton, 1985, and as mentioned in patent application US20020152501). Regeneration may also be obtained from plant calli, explants, organs, or parts thereof. Such regeneration techniques are well described in the state-of-the-art, such as by Klee et al. (Klee et al., Ann. Ver. of Plant Phys. 38:467-486, 1987, and as mentioned in patent application US20020152501). The plants thus transformed may be bred sexually or asexually, using methods known in the state-of-the-art, to provide successive generations of transgenic plants. (C. B Banchero et al., Difusao da Biotecnologia na Argentina e no Brasil: o caso das plantas transgenicas. [Biotechnology diffusion in Argentina and Brazil: the case of transgenic plants.] 1999. Instituto de Pesquisa de Relações Internacionais).

The RNA production in cells may be controlled through choice of the promoter sequence, through selection of the number of functional copies or through the integration site of the polynucleotides incorporated into the host genome. An organism may be transformed using the recombinant and/or expression vectors of the present invention containing one or more open reading frames for encoding a polypeptide of interest.

The isolated polynucleotide of the present invention is also useful in genome mapping, in physical mapping and in the positional cloning of genes. The sequence identified as SEQ ID NO:1 and its variants may be used to design oligonucleotide probes and primers. These oligonucleotide probes designed using the polynucleotide of the present invention may be used to detect the presence of the ubiquitin conjugating protein promoter in any organism containing sufficiently similar DNA sequences in their cells using techniques well known in the state-of-the-art, such as dot blot DNA hybridisation techniques (Sambrook, J., Fritsch, E. F., Maniatis, T. Molecular cloning: a laboratory manual. $2^{nd}$ edition [M]. New York: Cold Spring Harbor Laboratory Press, 1989).

The oligonucleotide primers designed using the polynucleotide of the present invention may be used for PCR amplifications. The polynucleotide of the present invention may also be used to tag or identify an organism or reproductive material of the latter. This tag may be obtained, for example, by the stable introduction in an organism of a heterologous, non-functional, non-disruptive, polynucleotide identifier controlled by the polynucleotide of the present invention.

EXAMPLES

The present invention is further defined by the following examples. It should be understood that these examples, although describing a part of the invention, are provided merely for illustrative purposes, and, therefore, in no way limit the scope of the present inventions.

Customary molecular biology techniques such as the transformation of bacteria and the electrophoresis of nucleic acids in agarose gel are referred to by the common terms used to describe them. Details of the practices of these techniques well known in the state-of-the-art are described in Sambrook, et al., (Molecular Cloning, A Laboratory Manual, 2nd ed. (1989), Cold Spring Harbor Laboratory Press). Several of the solutions used in the experimental manipulations are referred to by their common names such as "Agarose", "TBE", "Miniprep", etc. The composition of these solutions may be found referring to above mentioned Sambrook, et al.

Example 1

Isolation of the DNA Promoter Sequence for the Ubiquitin Conjugating Protein Gene for *Glycine max*

Extraction of DNA in soybean was performed using the DNeasy plant mini Kit 50 by QIAGEN. The DNA sequence responsible for expression of the ubiquitin conjugating protein gene was isolated from soybean plants using the "Tail-PCR" technique. "Tail-PCR" (Thermal Asymmetric Inter-Laced PCR) consists in applying the PCR (Polymerase Chain Reaction) technique to allow the isolation of the DNA segments adjacent to known sequences using specific sequential primers along with small randomly degenerated primers in a manner as to thermally control amplification efficiency related to specific and unspecific products (Liu, Y. & Whittier, R. F. (1995). Thermal asymmetric interlaced PCR: Automatable amplification and sequencing of insert end fragments from P1 and YAC clones for chromosome walking. Genomics 25, 674-681.)

Interspersing high and low stringency cycles, specific products are preferably amplified over non-specific products. Three PCR reactions were performed in sequence using three specific sequence primers on one side and a random primer on the other.

1) Primary Reaction:

200 ng of genomic soybean cv. 'Williams' DNA was added to 20 µl of a PCR reaction containing 20 mM Tris-HCl, 50 mM KCl, pH 8.4, (Gibco PCR buffer) 2 mM MgCl$_2$, 200 µM dNTPs, 400 nM primer UCE1 (5' GCTTGCCAATGGAA-CAT 3') (SEQ ID NO:2), 3 µM primer AD3 (5' WGTGNAG-WANCANAG 3') (SEQ ID NO:3), 1 U Taq DNA polymerase (Gibco). The reaction was performed in a thermocycler (Eppendorf, Mastercycler gradient) programmed to 38 cycles, with an initial stage of 1 min at 93° C., followed by the subsequent stages: 1 min at 95° C., 94° C., 55° C., 2.5 min at 72° C., return to stage 3 (1 min at 94° C.) repeat 4 times, 3 min at 25° C., 2.5 min at 72° C., 30 seconds at 94° C., 1 min at 60° C., 2.5 min at 72° C., return to the stage of 30 seconds at 94° C., repeat once, 30 seconds at 94° C., 1 min at 44° C., 2.5 min at 72° C., return to the stage of 30 seconds at 94° C., repeat 14 times, ending with 72° C. for 5 min.

2) Secondary Reaction:

1 µl of the product from the Primary Reaction was added to 20 µl of a PCR reaction containing 20 mM Tris-HCl, 50 mM KCl, pH 8.4, (Gibco PCR buffer) 2 mM MgCl$_2$, 200 M dNTPs, 400 nM primer UCE2 (5' AGRTCCTTIAGCTCCTT 3') (SEQ ID NO:4), 2 µM primer AD3 (5' WGTGNAGWAN-CANAG 3') (SEQ ID NO:5), 0.6 U Taq DNA polymerase (Gibco). The reaction was performed in a thermocycler (Eppendorf, Mastercycler gradient) programmed to 13 cycles, with an initial stage of 30 seconds at 94° C., followed by the subsequent stages: 1 min at 55° C., 2.5 min at 72° C., return to initial stage and repeat once, 94° C. for 30 seconds, 44° C. for 1 min, 72° C. for 2.5 min, return to initial stage and repeat 11 times, ending with 72° C. for 5 min.

3) Third Reaction:

1 µl of the product from the Secondary Reaction diluted 1/50 was added to 20 µl of a PCR reaction containing 20 mM Tris-HCl, 50 mM KCl, pH 8.4, (Gibco PCR buffer) 2 mM MgCl$_2$, 200 µM dNTPs, 400 nM primer UCE2 (5' AGRTC-CTTIAGCTCCTT 3') (SEQ ID NO:6), 1.5 µM primer AD3 (5' WGTGNAGWANCANAG 3') (SEQ ID NO:7), 0.6 U Taq DNA polymerase (Gibco). The reaction was performed in a thermocycler (Eppendorf, Mastercycler gradient) programmed to 24 cycles, with an initial stage of 1 min at 94° C., followed by the subsequent stages: 1 min at 44° C., 2.5 min at 72° C., return to initial stage and repeat once, return to initial stage and repeat 19 times, ending with 72° C. for 5 min.

Amplification with random primer AD3 produced a potentially positive fragment of approximately 1.2 kb (FIG. 1), based on the intensity of amplification and absence of primary reaction with TAIL-PCR.

Figure 2:
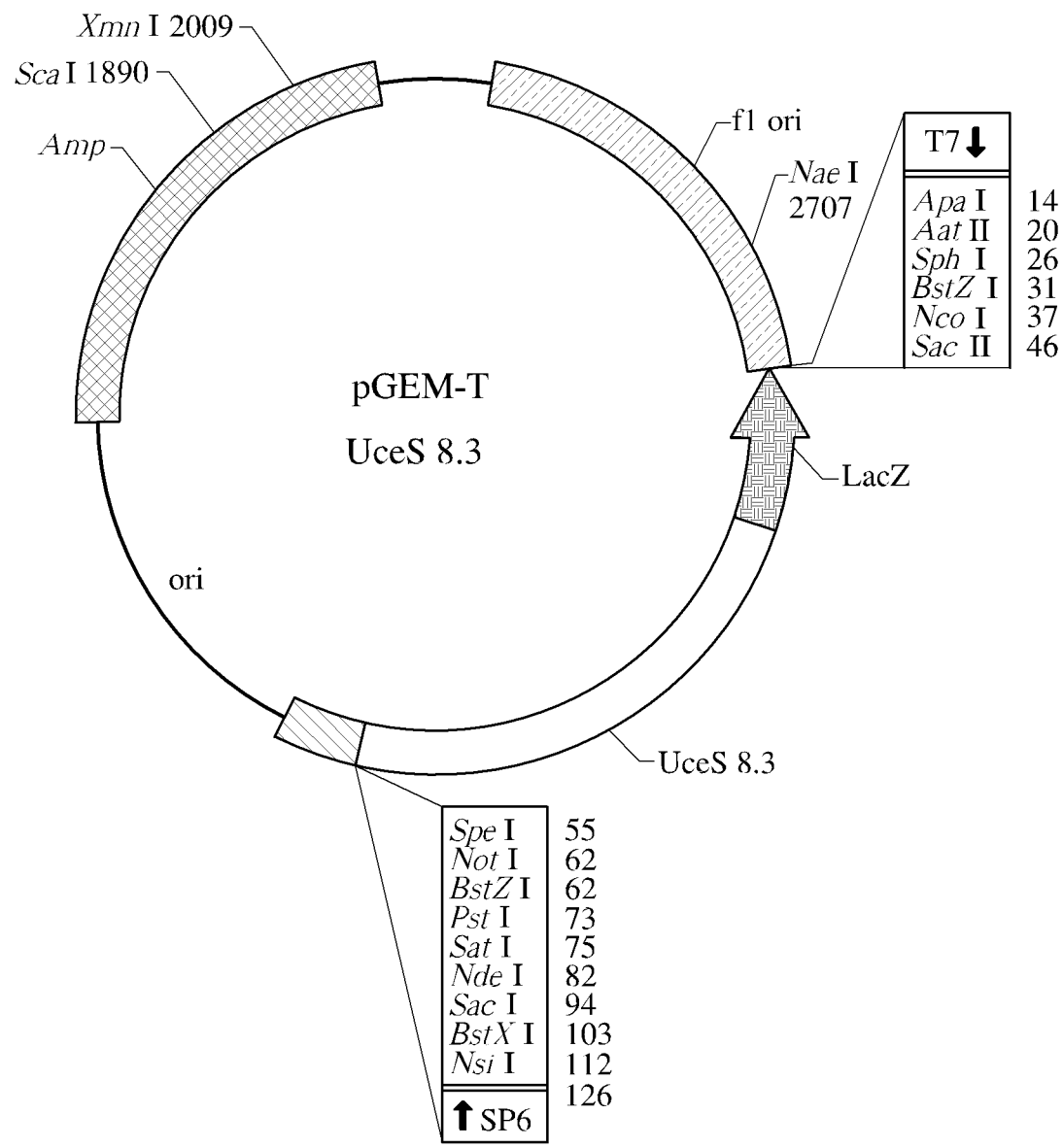
FIG. 2—pGEM-T vector linked to fragment of 1.2 kb.
Figure 3:
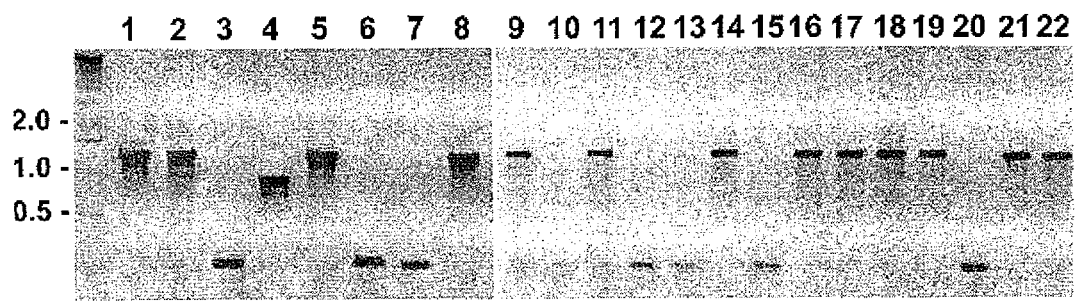
FIG. 3—Agarose gel from the cloning of the potentially positive amplified fragment of approximately 1.2 kb of soybean in vector pCR2.1. The numbers indicate each clone analysed. Clones 1, 2, 5, 8, 9, 11, 14, 16, 17, 18, 19, 21 and 22 are positive. The molecular mass marker (1 kb DNA-ladder, Gibco-BRL) is indicated in kb.

The product of the PCR was submitted to electrophoresis in agarose-TBE and the 1.2 kb amplified fragment was purified using the "Gene Clean" kit (QIAGEN) and cloned into the pGEM-T (Promega) vector. The resulting recombinant vector (FIG. 2) was used to transform cells of *E. coli* by electroporation (Manual de transformacao genetica de plantas. [Genetic Plant Trasnsformation Manual]. Brasilia: EMBRAPA-SPI/EMBRAPA-CENARGEM, 1998. p. 101). Fifty-three transformed clones were obtained. Twenty-two of these clones were selected for analysis by PCR with T7 and reverse primers. Thirteen of the clones presented inserts having the expected size of 1.2 kb (FIG. 3). Nine clones were selected for preparing small scale plasmid DNA (Miniprep—Sambrook, et al., (Molecular Cloning, A Laboratory Manual, 2nd ed. (1989), Cold Spring Harbor Laboratory Press) and for sequencing. The clones were sequenced in an ABI automatic sequencer using M13 reverse and M13 forward primers on the Embrapa-Cenargen sequencing platform.

Two clones were confirmed as positive by sequencing. The consensus sequence of the uce soybean promoter was obtained by the alignment of the 5 and 8 positive clones.

The analysis of the cloned soybean gene sequence corresponding to the Leubc4 gene family revealed the existence of a segment similar to the consensus TATA box usually present in eukaryote promoters. Furthermore, comparison of the sequences obtained with other sequences found in databases did not reveal any significant similarity, and neither were any significant open reading sequences detected which therefore indicates that the region does not correspond to a coding sequence.

Example 2

The comparative analysis of the uceS8.3 promoter sequence for the ubiquitin conjugating protein of soybean with other constitutive promoters of plants showed that the uceS8.3 promoter is significantly different from other promoters described in the literature (FIG. 4A-H).

Table 1 shows relatively low sequence identities between the main constitutive promoters described in the literature and the promoter of the present invention (uceS8.3). The promoters were selected from those with the greatest identity, in accordance with searches in the NCBI databases (ncbi.nlm.nih.gov).

TABLE 1

| Constitutive promoters | Organism | UceS8.3 (Identity in %) |
|---|---|---|
| Trehalose 6-phosphate synthase of *A. thaliana* | *Arabidopsis thaliana* | 35.2 |
| Uce_Oryza_3 | *Oryza sativa* | 21.4 |
| Gos-2_Zea | *Zea mays* | 24.3 |
| Uce_Oryza_1 | *Oryza sativa* | 38.3 |
| A-Tubulin_Coffea_1 | *Coffea* | 38.3 |
| Uce_Oryza_4 | *Oryza sativa* | 29.4 |
| UBI9_Saccharum | *Saccharum* | 41.5 |
| Enolase_Zea | *Zea mays* | 31.2 |
| Actin-2_Zea | *Zea mays* | 32.2 |
| Uce_Oryza_2 | *Oryza sativa* | 40.6 |
| A-Tubulin_Coffea_2 | *Coffea* | 42.7 |
| 35Sd_AMV | *Alfalfa mosaic virus* | 33.1 |

Table 1. Identity differences between the uceS8.3 soybean promoter and the different existing constitutive promoters.

The analysis was performed through the multiple alignment of sequences generated by the CLUSTAL_W software and pairing was done with the PAIRWISE software.

Example 3

Cloning of the uceS8.3 promoter sequence of the ubiquitin conjugating protein gene of soybean in a plant transforming vector (pCAMBIA1391).

Figure 5:
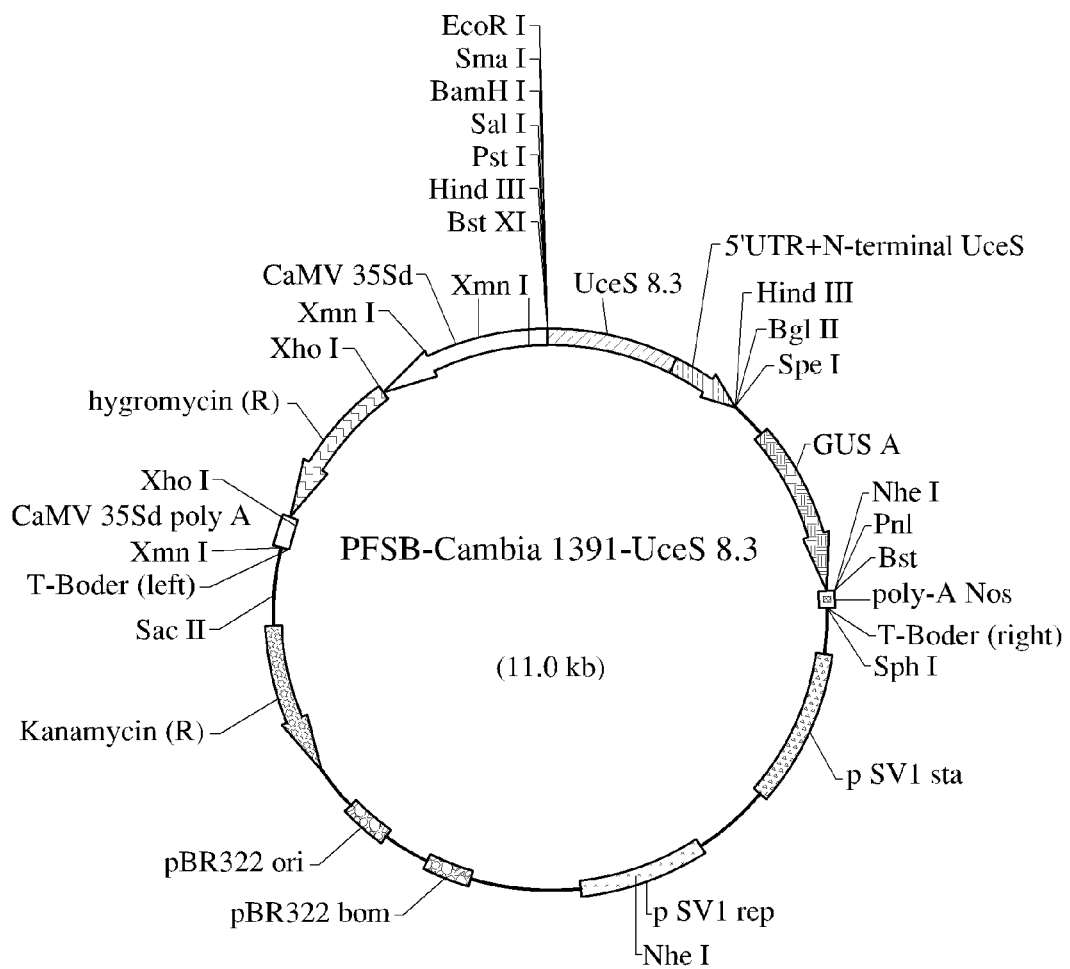
FIG. 5—Vector pCAMBIA1391Xc linked to the 1.2 kb insert. The figure shows a schematic representation of the pCAMBIA1391Xc plasmid: (a) containing double 35S promoter with the AMV (Alfalfa Mosaic Virus) enhancer together with GUS gene as a positive control, and (b) containing soybean promoter uceS8.3 (SEQ ID NO::1) of 1 kb, for transformation in *A. thaliana* in order to analyse the activity of soybean promoter uceS8.3.
Figure 6:
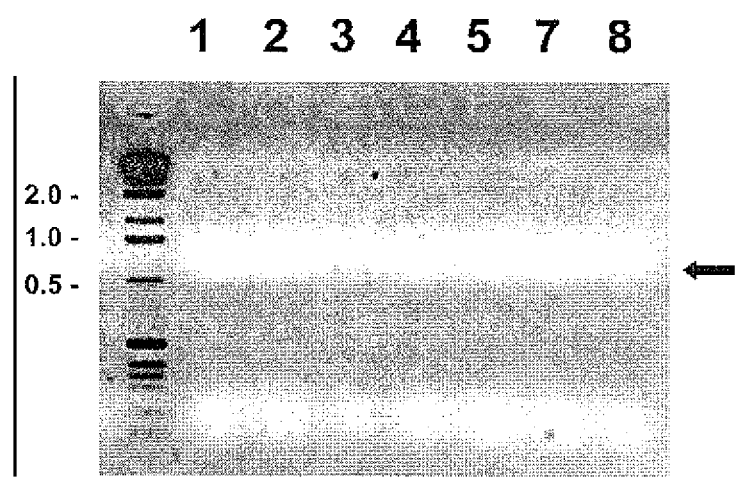
FIG. 6—Agarose gel image showing subcloning of the soybean promoter (clone uceS8) in vector pCAMBIA1391Xc. The numbers indicate the clone number of each clone analysed. Clones 3 and 8 are positive. The molecular mass marker is indicated in kb. The arrow points out the amplified fragment of approximately 1.2 kb.

The transformed bacteria DNA containing the recombinant vector, as such, the uce soybean promoter cloned to vector pGEM-T was digested with the restriction enzyme EcoPJ. Generally, 5 U of enzyme for every µg of DNA was used, in OPA buffer (One-Phor-All) by Pharmacia Biotech in a final concentration of 1×, at 37° C. for 3 hours. The enzyme site flanks the cloning site of the vector as well as the 1.2 kb insert purified with Gene Clean (Bio 101 System). Vector pCAMBIA1391Xc (FIG. 5) was digested with EcoRI, treated with alkaline phosphatase, CIP (Pharmacia Biotech) and purified with the Gene Clean kit (Bio 101 System). The 1.2 kb insert was linked to vector pCAMBIA1391Xc (FIG. 5) with T4 DNA ligase. The DNA concentration (vector pCAMBIA: promoter uce S8.3) used in the ligation system was performed at a molar rate of 1:3. The ligation reaction was performed in buffer of ligase 1× containing 5 U of T4 DNA and the recombinant and/or expression vector was used to transform competent cells of *E. coli* by electroporation (Manual de transformacao genetica de plantas. [Genetic Plant Trasnsformation Manual]. Brasilia: EMBRAPA-SPI/EMBRAPA-CENARGEM, 1998. p. 101). Eight clones were selected from a total of 693 and analysed by PCR, with AD3 and UCE2 primers, to ascertain the presence of the insert. Clones 3 and 8 were positive as shown by the 1.2 kb bands in FIG. 6. To ascertain the direction of the insert, the DNA of the 3 and 8 clones was obtained by preparation of small-scale plasmid DNA (Miniprep—Sambrook, et al., (Molecular Cloning, A Laboratory Manual, $2^{nd}$ ed. (1989), Cold Spring Harbor Laboratory Press) and digested with Hind III, that cuts the insert at position 641. Generally, 5 U of enzyme for every µg of DNA was used, in OPA buffer (One-Phor-All) by Pharmacia Biotech in a final concentration of 1×, at 37° C. for 3 hours. Clone uceS8.3 (uceS refers to the ubiquitin conjugating enzyme of soybean; the 8.3 or 8.8 refer to the positive clone number of obtained in each stage of the cloning process. The 8 corresponds to clone number 8 of the initial promoter amplification; the 3 and 8 refer to the clone numbers obtained in the cloning process of clone 8 in vector pCAMBIA1391Xc) presents the insert in a 'sense' orientation and clone uceS8.8 in an 'antisense' orientation. The pCAMBIA1391Xc vector was selected in order that the fragment corresponding to end 5' of the UCE gene present in clone uceS8.3 could be cloned in phase with the gusA gene sequence present in pCAMBIA1391Xc.

Example 4

Functional Characterisation of the DNA Promoter Sequence for the Ubiquitin Conjugating Protein Gene of Soybean—uceS8.3

In order to validate the potential of the DNA sequence isolated, the vector containing the promoter sequence SEQ ID NO:1 was introduced into *A. tumefasciens* LBA 4404 cells by heat shock. This transformation involved the addition of 1 µg of plasmid DNA (recombinant vector containing the promoter of the present invention) in 100µ of suspension of competent cells of *A. tumefaciens* LBA 4404 following which the reaction was incubated in ice for 30 minutes. The cells remained in liquid nitrogen until solidification and were then immediately transferred to 37° C. for a further incubation of 5 minutes. 1 mL YEB medium (5 g beef extract, 1 g yeast extract, 5 g peptone, 5 g sucrose and 240 mg MgSO, made up to the 1 liter with deionised water and with the pH adjusted to 6.8) was added to the reaction. The cells were then incubated for 2 hours at 28° C. The suspension was allowed to grow on solid YEB medium (YEB medium containing agar 1.6% p/v). A positive colony produced in the YEB medium with the antibiotic of choice (kanamycin) was selected. These transformed cells were used to transform *A. thaliana*-Columbia plants through the floral bud infiltration technique. This technique consists in soaking floral buds of *A. thaliana* in a culture of *Agrobacterium* containing 50 g/L (w/v) sucrose and 300 µL/L Silwet L-77. For such, the *A. thaliana* plants were immersed upside down during 5 minutes in a culture of *Agrobacterium* transformed with the recombinant vector of the present invention, in a manner, however, that only soaks the floral buds. The plants were then cultivated in greenhouse until seeds could be harvested.

Figure 8:
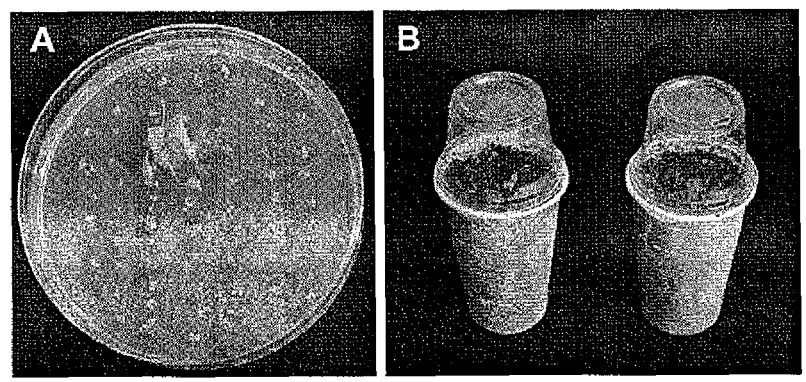
FIG. 8—*A. thaliana*-Columbia seeds and plants transformed with a vector containing the promoter sequence SEQ ID NO:1. Panel A shows seeds sown in MS culture medium with 20 µg/ml hygromycin to select for transformants containing pCAMBIA1391 vector with the sequence SEQ ID NO:1. Panel B shows germinating and rooted plantlets derived from transformed seeds in cups containing sterile soil and covered so as to retain humidity.
Figure 9:
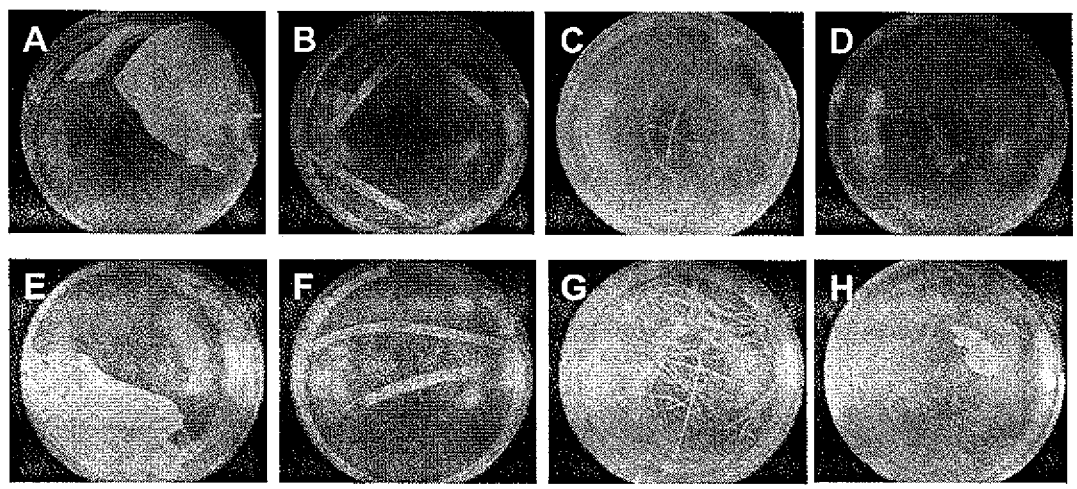
FIG. 9—A X-gluc assay showing β-glucoronidase expression from cuts of transformed *A. thaliana* plants. Panels A-D show gus gene expression in cuts taken from (A) leaves, (B) stem, (C) roots, and (D) floral buds of plants transformed with a vector containing the double CaMV35S (Cauliflower Mosaic Virus 35S promoter) with the sequence enhancer of the AMV (Alfalfa Mosaic Virus) (CaMV35SdAMV). Panels E-H show gus gene expression in cuts taken from gus gene expression in cuts taken from (E) leaves, (F) stem, (G) roots, and (H) floral buds of plants transformed with a vector containing a sense construction of the uceS8.3 soybean promoter with CaMV35SdAMV.

The seeds collected were first disinfested in alcohol 70% for 1 minute, then in sodium hypochlorite 1% for 15 minutes and finally washed 4 times with sterile water. The seeds were then sown in MS culture medium (Murashige, T. & Skoog, F. Physiol. Plant., 15: 473-497, 1962) containing hygromycin in a concentration of 20 µg/ml with the objective of selecting transformants (FIG. 8A). The germinating and rooted plantlets were transferred to cups containing sterile soil and covered so as to retain humidity before being transferred to greenhouses (FIG. 8B).

After several weeks, depending on the development of the acclimatised plants, cuts of roots, stems, leaves and floral buds were made and these were incubated in a solution of X-gluc prepared in accordance with Brasileiro & Carneiro (Manual de transformacao genetica de plantas. [Genetic Plant Transformation Manual]. Brasilia: EMBRAPA-SPI/EMBRAPA-CENARGEM, 1998. p. 131) with the intent of verifying the induction of gus gene expression.

The recombinant vector containing the double CaMV35S (Cauliflower Mosaic Virus 35S promoter) with the sequence enhancer of the AMV (Alfalfa Mosaic Virus) (CaMV35SdAMV) was capable of promoting expression of the gus gene in the (a) leaves, (b) stem, (c) roots and (d) floral buds of *A. thaliana* (FIG. 9 A-D), as expected, considering that this promoter has been described in the scientific literature as a strong constitutive promoter. Thus, when comparing the present invention containing a sense construction of the uceS8.3 soybean promoter with CaMV35SdAMV, it is possible to perceive that the uceS8.3 promoter is an excellent biotechnological tool because this latter promoter also possesses strong constitutive expression promoting widespread β-glucoronidase enzymatic activity in the (e) leaves, (f) stem, (g) roots and (h) floral buds of *A. thaliana* (FIG. 9E-H).

The strategy used in the present invention for the functional characterisation of the DNA sequences previously isolated from soybean plants was efficient to assess the potential of this sequence. The results obtained show that the uceS8.3 sequence is capable of conducting high levels of β-glucoronidase expression and thus represents a regulatory sequence having potential constitutive use for the production of genetically modified plants.

Figure 7:
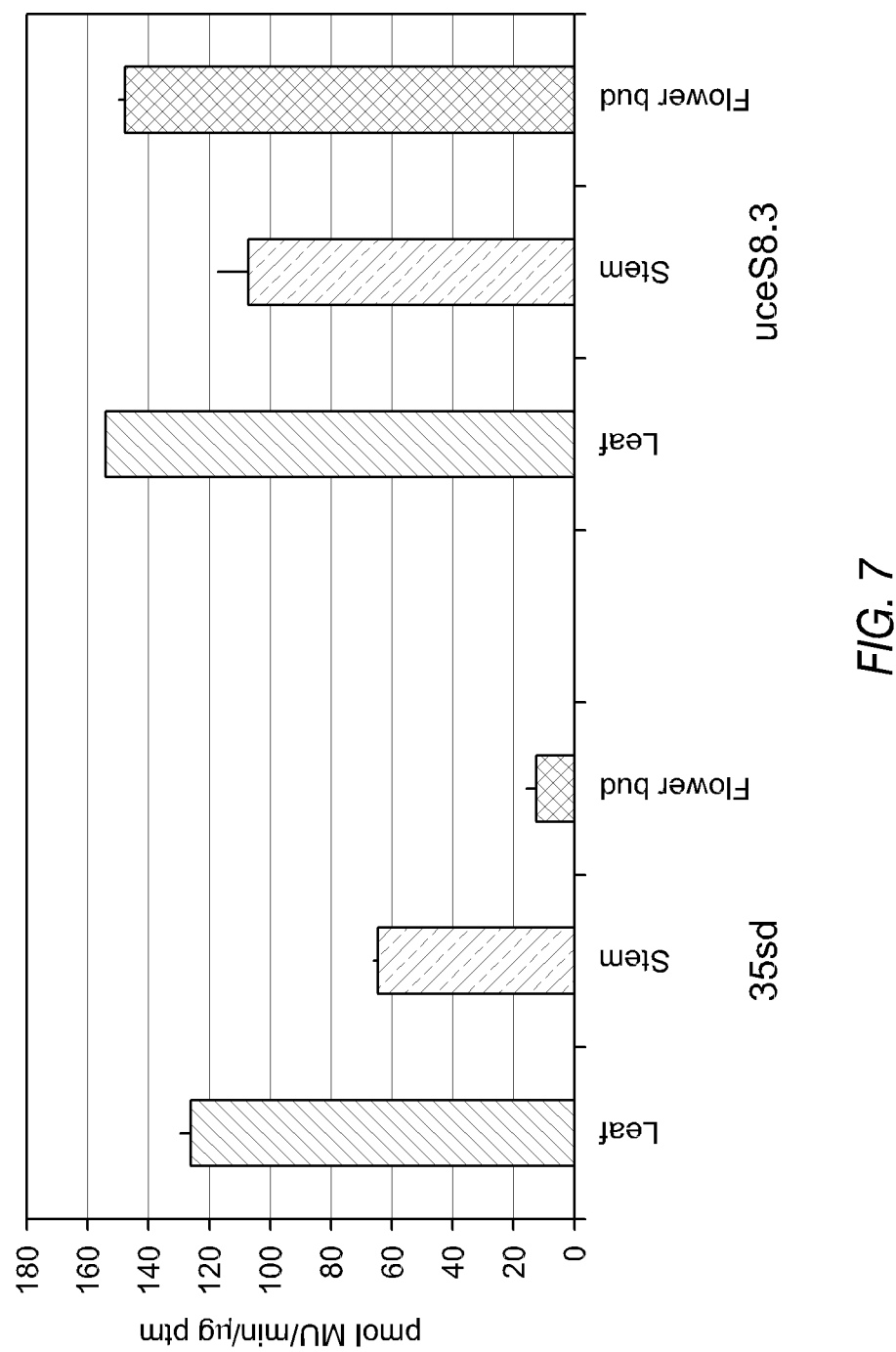
FIG. 7—Fluorimetric test of specific GUS activity in different parts of the *A. thaliana* plant (leaves, stem, flower bud) conducted by d35S and uceS8.3 promoters.

With the intent of quantitatively determining the expression conducted by the DNA sequence under study herein, a fluorimetric test was performed for specific β-glucoronidase enzyme activity using protein extracts from *Arabidopsis* plants containing the constructs (recombinant vectors) with CaMV35S (as positive control) and the uceS8.3 soybean promoter. For such, the protein extracts (were obtained in accordance with the Genetic Plant Transformation Manual (Manual de transformacao genetica de plantas. Brasilia: EMBRAPA-SPI/EMBRAPA-CENARGEM, 1998. p. 133) and were quantified by the Bradford method (in accordance to the Manual de transformacao genetica de plantas. [Genetic Plant Transformation Manual]. Brasilia: EMBRAPA-SPI/EMBRAPA-CENARGEM, 1998. p. 255) and submitted to 2 mM MUG (4-methyl-umbelliferyl-β-D-glucuronide) substrate and after 30 minutes of reaction at 37° C. the fluorimetric activity of the reaction was determined by means of spectrophotometric tests. The calculation of specific GUS activity was made in accordance to the Genetic Plant Transformation Manual (Manual de transformacao genetica de plantas. Brasilia: EMBRAPA-SPI/EMBRAPA-CENARGEM, 1998. p. 136. (FIG. 7).

It can be seen that the DNA sequence containing the uceS8.3 promoter region is capable of conducting GUS expression in leaves at levels similar to the strongest commercial plant promoters currently in use (double CaMV35S with the AMV enhancer). Furthermore, the expression conducted by this fragment in stems and, more specifically, in floral buds of *A. thaliana* plants is considerably superior to that of the CaMV35Sd+AMV promoter that therefore renders the promoter of the present invention more appropriate for the production of transgenic plants by expressing genes of interest in these plant tissues.

That which is claimed:

1. A non-naturally occurring chimeric gene comprising a first polynucleotide comprising SEQ ID NO:1 operably linked to a second polynucleotide.

2. The chimeric gene of claim 1, wherein said first polynucleotide is also operably linked to a third polynucleotide comprising an expression enhancer.

3. The chimeric gene of claim 2, wherein said second polynucleotide sequence comprises an encoding region that encodes a protein of interest.

4. The chimeric gene of claim 3, wherein said encoding region encodes a plant protein.

5. The chimeric gene of claim 3, wherein said encoding region is in sense orientation.

6. The chimeric gene of claim 2, wherein said expression enhancer comprises an enhancer sequence selected from the group consisting of the SV40 enhancer, the HSV-1 enhancer, the AMV enhancer, and the HPV-16 enhancer.

7. A recombinant vector comprising the chimeric gene of claim 1.

8. The chimeric gene of claim 4, wherein the second polynucleotide is operably linked to a termination sequence.

9. The chimeric gene of claim 8, wherein said termination sequence comprises a sequence selected from the group consisting of the SV40 termination signal, the HSV TK adenylation sequence, the nopaline synthase (NOS) gene termination signal of *Agrobacterium tumefasciens*, the octopine synthase gene termination signal, the 19S gene termination signal of CaMV, the 35S gene termination signal of CaMV, the alcohol dehydrogenase gene termination signal of maize, the manopine synthase gene termination signal, the beta-phaseolin gene termination signal, the ssRUBISCO gene termination signal, the sucrose synthase gene termination signal, and the trpC gene termination signal of *Aspergillus nidulans*.

10. The chimeric gene of claim 8, wherein said expression enhancer sequence comprises a sequence selected from the group consisting of the SV40 enhancer, the HSV-1 enhancer, the AMV enhancer, and the HPV-16 enhancer.

11. A transformed cell comprising the chimeric gene of claim 1 or the recombinant vector of claim 7.

12. A plant, a plant part, a propagulum, or progeny of said plant comprising the chimeric gene of claim 1 or the recombinant vector of claim 7.

13. A method for modifying gene expression in a plant comprising: stably incorporating within the genome of the plant the chimeric gene of claim 1 or the recombinant vector of claim 7.

14. A method for producing a plant having a modified gene expression comprising:
   a) transforming a plant cell, tissue, organ or embryo with the chimeric gene of claim 1, or the recombinant vector of claim 7;
   b) selecting transformed cells, cell calli, embryos or seeds;
   c) regenerating mature plants from said transformed cells, cell calli, embryos or seeds; and
   d) selecting said mature plants having a modified gene expression compared to non-transformed plants.

15. The chimeric gene of claim 3, wherein said encoding region is in anti-sense orientation.

* * * * *

SEQUENCE LISTING

```
<160> NUMBER OF SEQ ID NOS: 7

<210> SEQ ID NO 1
<211> LENGTH: 1171
<212> TYPE: DNA
<213> ORGANISM: Glycine max

<400> SEQUENCE: 1
tgtgtagaag cagagaaaac caaaagagta gtgaggaagc ccacttactt caaggacttt      60
gtctaaaggg tgaagtgtgt atttccataa caaaatcatc aacaaacaaa ttctgttact     120
aggattacta taaatacaat tgtaataaac aagcaaagat atgaatgaat gaaatttcca     180
tatttcttac ttttcttctt tggagggttc tggtcctcga aaccaaattc ttagttctct     240
taccaatttg tctcttttg gttggttatt cagtgtaaca aaataaaaaa aataagaatt     300
atgaatctaa ataatggtat acatgacaaa gagatatagc tcacattgac aactaaaaat     360
tgaattacta atcacttgca tttttcattta tcttttacac cagcgacaac caaattgatc     420
atacaacatt tgaaccaact tttcatgttt aattttctat gtgtaaccat atactgcata     480
gaggaccata catgtacctt ttgcatggtg catacacctc taacttatat tgtgaaaaca     540
agtttagttt ctatttgcta gtgttgtaca caatcaaatt tgttcttatc attcttttt     600 tttgtgtgaa agttacattc ttaaataagt attatggaat aagctttcat attacttaac     660
tttatttctt actcgttatt tcaaaaggtg aaaattacat ttctacccag acacacacta     720
aatacagtac aaactcgaag caaatgattt ggattgattt aaatcaattt taggttcaca     780
agggcaaggg gtggaatata aagaagaaag aaatggataa gggtgtcatt tggtgtgggc     840
atatatccaa ccaaaaaggg acattttgcg ggtatttgtg agtgtgtgag agagagagcg     900
agcagtttca gacacagaga gaggggtttg ggattggagg gattgacgct gcgtctcttc     960
ctcttctctt tcgatccatc cctcattcct aatcctccaa tccaaccacc tcagccccac    1020
actcacatat acacatgtct ctctctattt cccttttcac tttcactttc atttctaggg    1080
ttccgttctg atggctcttt cccttccaga tctgaacgcg tatcgtccct cctatggctt    1140
caaagcgcat cctcaaggag ctcaaggacc t                                   1171
```

```
<210> SEQ ID NO 2
<211> LENGTH: 17
<212> TYPE: DNA
<213> ORGANISM: Glycine max

<400> SEQUENCE: 2
gcttgccaat ggaacat                                                17

<210> SEQ ID NO 3
<211> LENGTH: 15
<212> TYPE: DNA
<213> ORGANISM: Artificial Sequence
<220> FEATURE:
<223> OTHER INFORMATION: Random degenerate primer
<220> FEATURE:
<221> NAME/KEY: misc_feature
<222> LOCATION: 5, 10, 13
<223> OTHER INFORMATION: n = a, t, c or g

<400> SEQUENCE: 3
wgtgnagwan canag                                                  15

<210> SEQ ID NO 4
<211> LENGTH: 17
<212> TYPE: DNA
<213> ORGANISM: Glycine max
<220> FEATURE:
<221> NAME/KEY: misc_feature
<222> LOCATION: 9
<223> OTHER INFORMATION: n = i

<400> SEQUENCE: 4
agrtccttna gctcctt                                                17

<210> SEQ ID NO 5
<211> LENGTH: 15
<212> TYPE: DNA
<213> ORGANISM: Artificial Sequence
<220> FEATURE:
<223> OTHER INFORMATION: Random degenerate primer
<220> FEATURE:
<221> NAME/KEY: misc_feature
<222> LOCATION: 5, 10, 13
<223> OTHER INFORMATION: n = a, t, c or g

<400> SEQUENCE: 5
wgtgnagwan canag                                                  15

<210> SEQ ID NO 6
<211> LENGTH: 17
<212> TYPE: DNA
<213> ORGANISM: Glycine max
<220> FEATURE:
<221> NAME/KEY: misc_feature
<222> LOCATION: 9
<223> OTHER INFORMATION: n = a, t, c or g

<400> SEQUENCE: 6
agrtccttna gctcctt                                                17

<210> SEQ ID NO 7
<211> LENGTH: 15
<212> TYPE: DNA
<213> ORGANISM: Artificial Sequence
<220> FEATURE:
<223> OTHER INFORMATION: Random degenerate primer
<220> FEATURE:
```

-continued

```
<221> NAME/KEY: misc_feature
<222> LOCATION: 5, 10, 13
<223> OTHER INFORMATION: n = a, t, c or g

<400> SEQUENCE: 7
wgtgnagwan canag                                                    15
```